US008799650B2

(12) United States Patent
Duma

(10) Patent No.: US 8,799,650 B2
(45) Date of Patent: Aug. 5, 2014

(54) SECURE PORTABLE MEDICAL INFORMATION SYSTEM AND METHODS RELATED THERETO

(75) Inventor: Christopher M. Duma, Newport Beach, CA (US)

(73) Assignee: Datcard Systems, Inc., Irvine, CA (US)

( * ) Notice: Subject to any disclaimer, the term of this patent is extended or adjusted under 35 U.S.C. 154(b) by 0 days.

(21) Appl. No.: 13/315,558

(22) Filed: Dec. 9, 2011

(65) Prior Publication Data

US 2012/0179908 A1     Jul. 12, 2012

Related U.S. Application Data

(60) Provisional application No. 61/422,103, filed on Dec. 10, 2010.

(51) Int. Cl.
*H04L 29/06* (2006.01)
(52) U.S. Cl.
USPC .............................................. 713/165; 705/3
(58) Field of Classification Search
USPC .............................. 713/165; 726/2, 27; 705/3
See application file for complete search history.

(56) References Cited

U.S. PATENT DOCUMENTS

| | | | |
|---|---|---|---|
| 4,149,239 A | 4/1979 | Jenkins et al. |
| 4,491,725 A | 1/1985 | Pritchard |
| 4,852,570 A | 8/1989 | Levine |
| 4,860,112 A | 8/1989 | Nichols |
| 4,874,935 A | 10/1989 | Younger |
| 4,945,410 A | 7/1990 | Walling |
| 4,958,283 A | 9/1990 | Tawara et al. |
| 5,002,062 A | 3/1991 | Suzuki |
| 5,005,126 A | 4/1991 | Haskin |
| 5,019,975 A | 5/1991 | Mukai |
| 5,208,802 A | 5/1993 | Suzuki |
| 5,235,510 A | 8/1993 | Yamada et al. |

(Continued)

FOREIGN PATENT DOCUMENTS

| | | |
|---|---|---|
| EP | 0684565 | 11/1995 |
| EP | 0781032 | 6/1997 |
| EP | 0952726 | 10/1999 |
| GB | 2096440 | 10/1982 |

OTHER PUBLICATIONS

European Response to the Communication Pursuant to Rule 161(1) and 162 EPC, dated May 13, 2011.

(Continued)

*Primary Examiner* — Ali Abyaneh
(74) *Attorney, Agent, or Firm* — Knobbe Martens Olson & Bear LLP

(57) ABSTRACT

Using a secure portable reference to medical information, stored on a portable storage medium, various embodiments allow a patient to give to their doctor an easy-to-use access key that will enable access to desired medical information stored on a computer network. The secure portable reference provides greater transportability of medical records to a patient or medical data repository including a doctor's office, clinic, or hospital, while maintaining data security to satisfy medical data privacy regulations and expectations. Some described embodiments use encrypted information inside the secure portable reference to hide, for example, who is allowed access to the stored medical information, and the network location of the stored information. Some embodiments use a secret PIN to authenticate the user attempting access to the referenced medical information. The secure portable reference contains information on network resources used to enable download access to medical information, including medical records and medical images.

14 Claims, 11 Drawing Sheets

(56) References Cited

U.S. PATENT DOCUMENTS

| | | | |
|---|---|---|---|
| 5,272,625 A | 12/1993 | Nishihara et al. |
| 5,291,399 A | 3/1994 | Chaco |
| 5,319,543 A | 6/1994 | Wilhelm |
| 5,319,629 A | 6/1994 | Henshaw et al. |
| 5,321,520 A | 6/1994 | Inga et al. |
| 5,321,681 A | 6/1994 | Ramsay et al. |
| 5,384,643 A | 1/1995 | Inga et al. |
| 5,410,676 A | 4/1995 | Huang et al. |
| 5,416,602 A | 5/1995 | Inga et al. |
| 5,451,763 A | 9/1995 | Pickett et al. |
| 5,469,353 A | 11/1995 | Pinsky et al. |
| 5,499,293 A | 3/1996 | Behram et al. |
| 5,513,101 A | 4/1996 | Pinsky et al. |
| 5,531,227 A | 7/1996 | Schneider |
| 5,542,768 A | 8/1996 | Rother et al. |
| 5,544,649 A | 8/1996 | David et al. |
| 5,586,262 A | 12/1996 | Komatsu et al. |
| 5,597,182 A | 1/1997 | Reber et al. |
| 5,597,995 A | 1/1997 | Williams |
| 5,605,153 A | 2/1997 | Fujioka et al. |
| 5,655,084 A | 8/1997 | Pinsky et al. |
| 5,659,741 A | 8/1997 | Eberhardt |
| 5,671,353 A | 9/1997 | Tian et al. |
| 5,687,717 A | 11/1997 | Halpern et al. |
| 5,721,825 A | 2/1998 | Lawson et al. |
| 5,724,582 A | 3/1998 | Pelanek et al. |
| 5,734,629 A | 3/1998 | Lee |
| 5,734,915 A | 3/1998 | Roewer |
| 5,763,862 A | 6/1998 | Jachimowicz et al. |
| 5,796,862 A | 8/1998 | Pawlicki et al. |
| 5,809,243 A | 9/1998 | Rostoker |
| 5,822,544 A | 10/1998 | Chaco et al. |
| 5,823,948 A | 10/1998 | Ross et al. |
| 5,832,488 A | 11/1998 | Eberhardt |
| 5,848,198 A | 12/1998 | Penn |
| 5,848,435 A | 12/1998 | Brant et al. |
| 5,859,628 A | 1/1999 | Ross et al. |
| 5,867,795 A | 2/1999 | Novis et al. |
| 5,867,821 A | 2/1999 | Ballantyne et al. |
| 5,869,163 A | 2/1999 | Smith et al. |
| 5,873,824 A | 2/1999 | Doi et al. |
| 5,882,555 A | 3/1999 | Rohde et al. |
| 5,884,271 A | 3/1999 | Pitroda |
| 5,899,998 A | 5/1999 | McGauley et al. |
| 5,909,551 A | 6/1999 | Tahara et al. |
| 5,911,687 A | 6/1999 | Sato et al. |
| 5,914,918 A | 6/1999 | Lee et al. |
| 5,924,074 A | 7/1999 | Evans |
| 5,942,165 A | 8/1999 | Sabatini |
| 5,946,276 A | 8/1999 | Ridges |
| 5,950,207 A | 9/1999 | Mortimore |
| 5,982,736 A | 11/1999 | Pierson |
| 5,995,077 A | 11/1999 | Wilcox |
| 5,995,345 A | 11/1999 | Overbo |
| 5,995,965 A | 11/1999 | Experton |
| 6,006,191 A | 12/1999 | DiRienzo |
| 6,014,629 A | 1/2000 | DeBruin-Ashton |
| 6,021,404 A | 2/2000 | Moukheibir |
| 6,022,315 A | 2/2000 | Iliff |
| 6,032,120 A | 2/2000 | Rock et al. |
| 6,041,703 A | 3/2000 | Salisbury et al. |
| 6,067,075 A | 5/2000 | Pelanek |
| 6,131,090 A | 10/2000 | Basso, Jr. et al. |
| 6,148,331 A | 11/2000 | Parry |
| 6,149,440 A | 11/2000 | Clark et al. |
| 6,155,409 A | 12/2000 | Hettinger |
| 6,241,668 B1 | 6/2001 | Herzog |
| 6,260,021 B1 | 7/2001 | Wong |
| 6,272,470 B1 | 8/2001 | Teshima |
| 6,278,999 B1 | 8/2001 | Knapp |
| 6,283,761 B1 | 9/2001 | Joao |
| 6,363,392 B1 | 3/2002 | Halstead et al. |
| 6,397,224 B1 | 5/2002 | Zubeldia et al. |
| 6,415,295 B1 | 7/2002 | Feinberg |
| 6,421,650 B1 | 7/2002 | Goetz |
| 6,564,256 B1 | 5/2003 | Tanaka |
| 6,591,242 B1 | 7/2003 | Karp et al. |
| 6,671,714 B1 | 12/2003 | Weyer et al. |
| 6,934,698 B2 | 8/2005 | Judd |
| 6,954,802 B2 | 10/2005 | Sutherland et al. |
| 7,162,571 B2 | 1/2007 | Kilian et al. |
| 7,213,022 B2 | 5/2007 | Whelan et al. |
| 7,240,150 B1 | 7/2007 | Todd et al. |
| 7,266,556 B1 | 9/2007 | Coates |
| 7,298,836 B2 | 11/2007 | Wellons et al. |
| 7,366,836 B2 | 4/2008 | Todd et al. |
| 7,379,605 B1 | 5/2008 | Ticsa |
| 7,398,391 B2 | 7/2008 | Carpentier et al. |
| 7,415,731 B2 | 8/2008 | Carpentier et al. |
| 7,428,611 B1 | 9/2008 | Todd et al. |
| 7,434,057 B2 | 10/2008 | Yagawa |
| 7,475,432 B2 | 1/2009 | Carpentier et al. |
| 7,487,551 B2 | 2/2009 | Carpentier et al. |
| 7,523,489 B2 | 4/2009 | Bossemeyer et al. |
| 7,530,115 B2 | 5/2009 | Carpentier et al. |
| 7,539,813 B1 | 5/2009 | Todd et al. |
| 7,546,486 B2 | 6/2009 | Slik et al. |
| 7,552,340 B2 | 6/2009 | Ooi et al. |
| 7,552,356 B1 | 6/2009 | Waterhouse et al. |
| 7,590,672 B2 | 9/2009 | Slik et al. |
| 7,591,022 B2 | 9/2009 | Carpentier et al. |
| 7,621,445 B2 * | 11/2009 | Esseiva et al. ............... 235/380 |
| 7,640,271 B2 | 12/2009 | Logan, Jr. |
| 7,657,581 B2 | 2/2010 | Orenstein et al. |
| 7,694,331 B2 | 4/2010 | Vesikivi et al. |
| 7,734,603 B1 | 6/2010 | McManis |
| 7,797,546 B2 | 9/2010 | Kendon |
| 7,836,493 B2 | 11/2010 | Xia et al. |
| 7,865,735 B2 * | 1/2011 | Yiachos ...................... 713/182 |
| 8,045,214 B2 | 10/2011 | Samari |
| 8,059,304 B2 | 11/2011 | Samari |
| 2001/0027402 A1 | 10/2001 | Ramsaroop |
| 2002/0010679 A1 | 1/2002 | Felsher |
| 2002/0083030 A1 | 6/2002 | Yang et al. |
| 2002/0085476 A1 | 7/2002 | Samari-Kermani |
| 2002/0103675 A1 | 8/2002 | Vanelli |
| 2002/0103811 A1 | 8/2002 | Frankhauser et al. |
| 2002/0138524 A1 | 9/2002 | Ingle et al. |
| 2003/0005464 A1 | 1/2003 | Gropper et al. |
| 2003/0040940 A1 | 2/2003 | Nehammer |
| 2003/0069752 A1 * | 4/2003 | LeDain et al. .................... 705/2 |
| 2003/0220822 A1 | 11/2003 | Fiala et al. |
| 2004/0006492 A1 | 1/2004 | Watanabe |
| 2004/0078236 A1 | 4/2004 | Stoodley et al. |
| 2004/0083123 A1 | 4/2004 | Kim et al. |
| 2004/0187012 A1 * | 9/2004 | Kohiyama et al. ............ 713/193 |
| 2004/0187027 A1 | 9/2004 | Chan |
| 2004/0199762 A1 | 10/2004 | Carlson et al. |
| 2004/0210458 A1 | 10/2004 | Evans et al. |
| 2005/0075909 A1 | 4/2005 | Flagstad |
| 2005/0086082 A1 | 4/2005 | Braunstein et al. |
| 2005/0125252 A1 | 6/2005 | Schoenberg |
| 2005/0125254 A1 | 6/2005 | Schoenberg |
| 2005/0125258 A1 | 6/2005 | Yellin et al. |
| 2005/0144172 A1 | 6/2005 | Kilian et al. |
| 2005/0192837 A1 | 9/2005 | Fears et al. |
| 2005/0197859 A1 | 9/2005 | Wilson et al. |
| 2005/0267863 A1 | 12/2005 | Carpentier et al. |
| 2006/0080307 A1 | 4/2006 | Carpentier et al. |
| 2006/0085226 A1 | 4/2006 | Kamber |
| 2006/0155584 A1 | 7/2006 | Aggarwal |
| 2006/0179112 A1 | 8/2006 | Weyer et al. |
| 2006/0242144 A1 | 10/2006 | Esham et al. |
| 2007/0027715 A1 | 2/2007 | Gropper et al. |
| 2007/0061170 A1 | 3/2007 | Lorsch |
| 2007/0180509 A1 | 8/2007 | Swartz et al. |
| 2007/0289024 A1 * | 12/2007 | Mohammed ..................... 726/28 |
| 2008/0005030 A1 | 1/2008 | Schlarb et al. |
| 2008/0013365 A1 | 1/2008 | Yueh |
| 2008/0065718 A1 | 3/2008 | Todd et al. |
| 2008/0071577 A1 | 3/2008 | Highley |
| 2008/0183719 A1 | 7/2008 | Kageyama et al. |
| 2008/0208919 A1 | 8/2008 | I Dalfo et al. |
| 2008/0222654 A1 | 9/2008 | Xu et al. |

(56) References Cited

U.S. PATENT DOCUMENTS

| | | | |
|---|---|---|---|
| 2008/0244196 | A1 | 10/2008 | Shitomi et al. |
| 2008/0285759 | A1 | 11/2008 | Shaw |
| 2008/0313236 | A1 | 12/2008 | Vijayakumar et al. |
| 2008/0319798 | A1 | 12/2008 | Kelley |
| 2009/0043828 | A1 | 2/2009 | Shitomi |
| 2009/0055924 | A1 | 2/2009 | Trotter |
| 2009/0089335 | A1 | 4/2009 | Shitomi et al. |
| 2009/0119764 | A1 | 5/2009 | Applewhite et al. |
| 2009/0132775 | A1 | 5/2009 | Otani et al. |
| 2009/0157987 | A1 | 6/2009 | Barley |
| 2009/0198515 | A1 | 8/2009 | Sawhney |
| 2009/0204433 | A1 | 8/2009 | Darian et al. |
| 2009/0219411 | A1 | 9/2009 | Marman et al. |
| 2009/0240764 | A1 | 9/2009 | Peleg et al. |
| 2009/0252480 | A1 | 10/2009 | Wright |
| 2009/0319736 | A1 | 12/2009 | Otani et al. |
| 2010/0138446 | A1 | 6/2010 | Canessa et al. |
| 2010/0174750 | A1 | 7/2010 | Donovan et al. |
| 2010/0286997 | A1 | 11/2010 | Srinivasan |

OTHER PUBLICATIONS

Ferelli, Mark, Content-addressable storage—Storage as I See it, Computer Technology Review, http://findarticles.com/p/articles/mi_m0BRZ/is_10_22/ai_98977101/, Oct. 2002, in 2 pages.

Menezes A et al.: "Handbook of Applied Cryptography, Key Management Techniques" Handbook of Applied Cryptography, Jan. 1, 1996, pp. 543-590.

HoneyComb Fixed Content Storage, Solaris, http://hub.opensolaris.org/bin/view/Project+honeycomb/Webhome, Oct. 26, 2009 in 2 pages.

International Search Report and Written Opinion issued in PCT/US2009/054799, dated Nov. 16, 2009.

International Search Report and Written Opinion issued in PCT/US2009/061890, dated Dec. 10, 2009.

International Search Report and Written Opinion issued in PCT/US2011/033647, dated Nov. 28, 2011.

International Search Report and Written Opinion issued in PCT/US2011/063987, dated Sep. 6, 2012.

Mellor, Chris, Making a Hash of File Content, Techworld, http://features.techworld.com/storage/235/making-a-hash-of-file-content/?, Dec. 3, 2009, in 2 pages.

Quinlan, S., et al., Venti: a new approach to archival storage, doc.cat-v.org/plan_9/4th_edition/papers/venti, in 20 pages.

Rhea, S., et al., Fast, Inexpensive Content-Addressed Storage in Foundation, http://doc.cat-v.org/plan_9/misc/foundation/, in 22 pages.

Fintan J McEvoy et al.: "Security of Patient and Study Data Associated with DICOM Images when Transferred Using Compact Disc Media" Journal of Digital Imaging; The Journal of the Society for Computer Applications in Radiology, vol. 22, No. 1, Aug. 21, 2007 (pp. 65-70).

Tolia, N., et al., Opportunistic Use of Content Addressable Storage for Distributed File Systems, USENIX Association, Jun. 9, 2003, in 15 pages.

Medical Imaging Magazine, Jan. 2000. Product Showcase, Automated Dicom Exchange Station. 1 page.

Terry May Titled "Medical Information Security: the Evolving Challenege" copyright 1998 IEEE doc #0-7803-4535-5/98 pp. 85-92.

Ted Cooper Titled "Kaiser Permanente Anticipates High Cost as it Gears up for HIPAA" IT Health Care Strategist vol. 1, No. 10 Oct. 1999 p. 4.

Haufe G. et al.: PACS at Work: A Multimedia E-Mail Tool for the Integration of Voices and Dynamic Annotation, Computer Assisted Radiology, Proceedings of the International Symposium, 1998 Etsevier Science B.V., pp. 417-420.

Dimitroff D C et al: "An Object Oriented Approach to Automating Patient Medical Records" Proceedings of the International Computer Software and Applications Conference. (Compsac), US, Washington, IEEE. Comp. Soc. Press, vol. CONF. 14, 1990, pp. 82-87.

Kleinholz L et al: "Multimedia and PACS. Setting the Platform for Improved and New Medical Services in Hospitals and Regions" Car '96 Computer Assisted Radiology. Proceedings of the International Symposium on Computer and Communication Systems for Image Guided Diagnosis and Therapy, Paris, France, Jun. 1996, pp. 313-322, XP002083080 1996, Amsterdam, Netherlands, Elsevier, Netherlands, ISBN: 0-444-82497-9.

1996 Annual HIMSS Conference and Exhibition, Managing Care: The Race is on, dated Mar. 3-7, 1996.

FlimX Presentation Slides.

Candelis website excerpt, http://www.candelis.com via the Internet Wayback Machine (Archive.org), Jul. 19, 2010.

Carestream website excerpt, http://carestreamhealth.com via the Internet Wayback Machine (Archive.org), Nov. 20, 2010.

eMix website excerpt, http://www.emix.com via the Internet Wayback Machine (Archive.org), Jul. 10, 2011.

GE Healthcare IT website excerpt, http://www.dynamic-imaging.com via the Internet Wayback Machine (Archive.org), Jan. 27, 2010.

HeartIT website excerpt, http://heartit.com via the Internet Wayback Machine (Archive.org), Jan. 29, 2009.

Infinitt North America website excerpt, http://infinittna.com via the Internet Wayback Machine (Archive.org), Feb. 28, 2009.

LifeImage website excerpt, http://www.lifeimage.com via the Internet Wayback Machine (Archive.org), Nov. 4, 2010.

McKesson website excerpt, http://www.mckesson.com via the Internet Wayback Machine (Archive.org), Oct. 20, 2010.

MyMedicalRecords.com website excerpt, http://www.mymedicalrecords.com via the Internet Wayback Machine (Archive.org), Aug. 1, 2010.

PACS Image website excerpt, http://www.pacsimage.com via the Internet Wayback Machine (Archive.org), Apr. 2, 2010.

ScImage website excerpt, http://www.scimage.com via the Internet Wayback Machine (Archive.org), Sep. 27, 2010.

See My Radiology website excerpt, http://www.seemyradiology.com via the Internet Wayback Machine (Archive.org), Jul. 11, 2010.

Symantec Health Press Release, http://www.symantec.com/about/news/release/article.jsp?prid=20100819_01, Aug. 19, 2010.

XrayLine website excerpt, http://www.xrayline.com via the Internet Wayback Machine (Archive.org), Oct. 13, 2010.

* cited by examiner

SECURE PORTABLE MEDICAL INFORMATION SYSTEM AND METHODS RELATED THERETO

CROSS-REFERENCE TO RELATED APPLICATIONS

This non-provisional application claims a benefit of priority of the provisional patent application Ser. No. 61/422,103, titled "Secure Portable Medical Information Access System and Method" and filed Dec. 10, 2010, the disclosure of which is incorporated herein by reference in its entirety.

BACKGROUND

1. Field

This disclosure relates to devices, systems, and secure methods of distributing private medical information among doctors, patients, imaging centers, medical centers, treatment centers, and hospitals, and more specifically, distribution of medical images to consulting physicians.

2. Description of the Related Art

Hospitals and doctors' offices are the stewards of private patient medical information. Every time a patient visits a doctor, clinic or hospital, their private personal and medical information is recorded. The personal and medical information is stored in hospital databases, which can consist of picture archiving and communication systems ("PACS"), relational databases, content addressable storage systems, and computer files, among other storage methods.

Under certain likely scenarios, this personal and medical information must be accessible by medical personnel outside of the doctor's office or hospital. It is not uncommon for a hospital to seek outside expert doctors to consult on interpreting lab results and medical images to improve chances of diagnosis. These outside doctors require access to the medical information databases inside the doctor's offices and hospitals to make their diagnosis and perform their job. Similarly, a patient may seek an outside doctor's advice herself, either to see a specialist in a field, or to get a second opinion.

One option is to grant electronic access to the patient's information, but current hospital access systems have a number of issues. Hospitals are reluctant to grant access to their databases to outside doctors automatically, and often require that even internal doctors fill out paperwork, apply for access, and wait long periods before access is available. Further, many medical facilities require their doctors to remember and type into their computer complicated Uniform Resource Locator (URL) strings. Moreover, there is a lack of seamless access to the medical information held or controlled by a doctor, clinic, hospital, a third-party imaging center, or in any cloud-based medical data repository (collectively referred to as "MDRs"). MDRs are reluctant to provide seamless access to client entities for several reasons.

One reason MDRs are reluctant to provide seamless access to client entities is that MDRs contain private personal information. Unless an MDR restricts access to this information, the unauthorized release of a person's medical history and images could violate the patient's privacy and cause severe embarrassment. Thus, MDRs restrict access to a patient's medical records to small set of users, and carefully scrutinize any users applying for access to the information.

Another issue is that MDRs must comply with all current and future health information laws and regulations. One such federal regulation scheme is the Health Insurance Portability and Accountability Act (HIPAA) which regulates the use and disclosure of Protected Health Information. The regulations may require any access to equipment containing health information to be carefully controlled and monitored. Access to hardware and software must be limited to properly authorized individuals in some cases. HIPAA also may require authentication of any entity that communicates with an MDR, such as authentication through the use of corroborating password systems, two or three-way handshakes, telephone callback procedures, and token systems. HIPAA also seeks to ensure that the data within an MDR's systems have not been altered or accessed in an unauthorized manner. Any violation of HIPAA can result in an investigation by federal authorities and civil money penalties.

Thus, MDRs are reluctant to grant access to their electronic records. An outside doctor who requires access to patient medical information databases inside an MDR must often wait for months or years while an investigation occurs and clearance procedures are performed. Consequently, many outside doctors avoid applying for direct access to hospital databases, and instead seek other methods of access to their patient's medical information.

Some doctors seek a physical delivery of electronic records to their offices for evaluation. These electronic records are often transported on a CD-ROM, DVD, or other portable storage media such as a USB key, memory card or stick, flash drive, thumb drive, optical disc, or portable disk drive. Either the patient requests the records from their MDR and supplies them for the doctor, or the doctor can acquire the portable media directly from the MDR. The doctor then can load the images from the portable media onto his local computer and use them for diagnosis.

There are numerous problems with accessing the medical information in this manner. Portable media has limited storage capacity, and the size of medical records and medical images have grown substantially. For example, image formats often are comprised of multiple 2D slice images to create a 3D image, growing an image files size. Further, if the images contain fourth dimension time information, the file sizes can grow rapidly. Thus, the larger hi-tech medical images may not be able to be transported by portable media, or would require additional portable media that consumes additional time, cost, and effort to create. Further, portable media is often accessed at a slow rate compared to permanent media such as a hard drive. Thus, it may take a while for the media to load on the doctor's computer.

A doctor might also try to access a patient's medical information through an electronic network such as the Internet. For example, an MDR may give out a specific URL for a doctor to use to gain access. However, because HIPAA and other laws and regulations may prohibit the sending of a URL that grants access to medical information through email or another near-instant electronic communication method due to the lack of data security, a long URL must be communicated to the doctor by voice or printout. A URL string is usually very long, and thus it takes a significant amount of time for the doctor to enter and manually type such a URL into his web browser. Further, human copying and manual data entry increases the chance to transpose characters or create errors in the URL that prevent access to the data and create user frustration.

Thus, a method of access that is responsive to the needs of security, health information laws and regulations, and ease of access is desired. These and other problems are addressed by the embodiments described below.

SUMMARY

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Embodiments of the apparatus, systems, methods, kits, computer readable media, and devices described below overcome problems of the prior art and enable secure, portable, seamless access to a patient's personal and medical information.

A secure portable reference to individual patient medical data provides a compact, secure, seamless method for a person or entity, including patients or doctors, to access online personal and medical information. The secure portable reference may be a data format and network access device embodied in various methods, apparatus, devices, computer readable media, or kits. For example, in one embodiment, when a patient or doctor requires online access to medical information held or controlled by an MDR, the MDR provides an encrypted set of data including a link URL, an identification number for the patient, a hospital identifier, a timestamp, and records this information into a file or files on a portable storage media or device, such as a USB thumb drive. The secure portable reference may also be transmitted via email to the patient or doctor, for example as an attachment to the email or within the body of the email itself. The secure portable reference may also be in the form of a bar code. Also included on the portable storage media or device is a linking module similar to a web-browser, and a security program that can decrypt the reference set of data. In this embodiment, the entire set of data on the portable storage media or device is called a secure portable reference.

The encrypted data is encrypted using a personal identification number (PIN) told to or selected by the patient or doctor. By entering the PIN, the security module can decrypt the encrypted portion of the secure portable reference and make it accessible by the linking module.

After decryption, the linking module, which runs on a client computing device, then opens the link URL in the reference set of data, and requests the MDR website or Internet resource contained within the URL. The website then authenticates the patient or doctor by having the user enter their PIN. If the PIN matches the data stored by the MDR, the website allows access to the medical records. The medical records, along with an optional imaging viewing program, are then downloaded by the user to the client computer for consumption.

These and other features and advantages of the devices, systems, and methods for a secure portable reference will become apparent from the following description of embodiments. Neither this summary nor the following detailed description purports to define all possible embodiments.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures.

DETAILED DESCRIPTION

Figure 1:
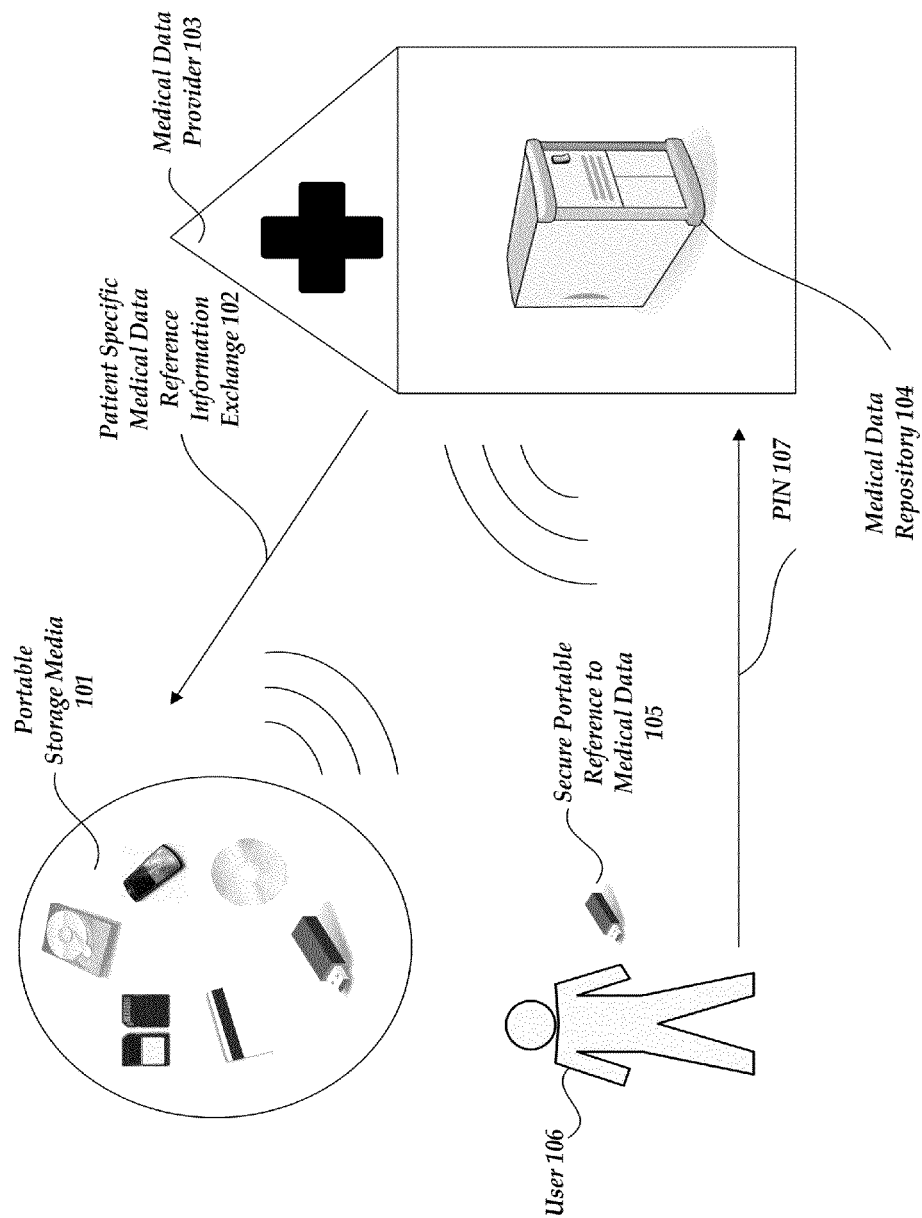
FIG. 1 illustrates an abstract representation of the exemplary creation process of a secure portable reference to individual patient medical data.

Although several embodiments, examples and illustrations are disclosed below, it will be understood by those of ordinary skill in the art that the invention described herein extends beyond the specifically disclosed embodiments, examples and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

In the following detailed description, references are made to the accompanying drawings that illustrate specific embodiments in which embodiments may be practiced. Electrical, mechanical, programmatic and structural changes may be made to the embodiments without departing from the spirit and scope of the disclosure.

Unless indicated otherwise, terms as used herein will be understood to imply their customary and ordinary meaning. Personal information is a broad term and is to be given its ordinary and customary meaning to a person of ordinary skill in the art (i.e., it is not to be limited to a special or customized meaning) and includes, without limitation, Social Security Number, address, phone number, email address, credit card numbers, bank accounts, and medical bills, and further would include identifying and person information relating to a particular person.

PIN is a broad term and is to be given its ordinary and customary meaning to a person of ordinary skill in the art (i.e., it is not to be limited to a special or customized meaning) and includes, without limitation, any combination of alphanumeric characters and symbols, including but not limited to numbers 0-9, letters A-Z, letters a-z, non-standard characters such as !@#&*, ASCII and non-ASCII characters, and may be of varying lengths and requirements.

Medical information is a broad term and is to be given its ordinary and customary meaning to a person of ordinary skill in the art (i.e., it is not to be limited to a special or customized meaning) and includes, without limitation, images, exams, studies, lab results, test results, medical history, payment information, billing information, prescriptions and diagnoses, among other information.

Medical Data Repository ("MDR") is a broad term and is to be given its ordinary and customary meaning to a person of ordinary skill in the art (i.e., it is not to be limited to a special or customized meaning) and includes, without limitation, any medical data repository, database, or storage media, including cloud-based data repositories, which store medical information typically controlled by, for example, doctors, clinics, hospitals, or third-party imaging centers.

Medical images is a broad term and is to be given its ordinary and customary meaning to a person of ordinary skill in the art (i.e., it is not to be limited to a special or customized meaning) and includes, without limitation, magnetic resonance imaging, positron emission tomography, photo acoustic imaging, thermography, computed tomography, ultrasonography, and angiography among others stored in a digital imaging and communications in medicine ("DICOM") or non-DICOM format. These images can represent medical information in up to four dimensions, and often require large amounts of data storage.

Portable electronic device is a broad term and is to be given its ordinary and customary meaning to a person of ordinary skill in the art (i.e., it is not to be limited to a special or customized meaning) and includes, without limitation, cell phones; smart phones; mobile phones; BlackBerry devices; personal digital assistants (PDAs); multimedia electronic devices, including for example MP3 players, iPods, iPod Touch, or similar device for consuming media content; tablet personal computers, including but not limited to tablets like iPad, Kindle Fire, Nook Tablet, and any portable device running a mobile operating system, such as but not limited to iOS, Android, and Windows; notebook computers; laptop computers; and any type of mobile electronic device in general.

Bar code is a broad term and is to be given its ordinary and customary meaning to a person of ordinary skill in the art (i.e., it is not to be limited to a special or customized meaning) and includes, without limitation, machine-readable bar code, radio-frequency identification ("RFID"), quick-response ("QR") codes, or any other form of computer or machine readable bar code.

Scanning software and scanning devices are broad terms and are to be given their ordinary and customary meanings to a person of ordinary skill in the art (i.e., it is not to be limited to a special or customized meaning) and includes, without limitation, cameras, scanners, portable electronic devices equipped with a camera or scanner, computing systems connected to or with the ability to connect to a camera or scanner, computer programs or software modules configured to scan, read, and/or decrypt a bar code, or any other computing device that may be configured to scan, read, and/or decrypt a bar code.

Details regarding several illustrative preferred embodiments for implementing the system and method described herein are described below with reference to the figures. At times, features of certain embodiments are described below in accordance with that which will be understood or appreciated by a person of ordinary skill in the art to which the system and method described herein pertain. For conciseness and readability, such a "person of ordinary skill in the art" is often referred to as a "skilled artisan."

Various embodiments overcome one or more issues with the prior art. Other embodiments may overcome different issues with the prior art. For example, some of the embodiments herein provide for seamless access to medical data held by MDRs. Other embodiments provide for secure access to medical data held by MDRs. Other embodiments provide for both seamless and secure access.

It will be apparent to a skilled artisan, in light of this disclosure, that the devices, systems, and methods described herein can advantageously be implemented using computer software, hardware, firmware, or any combination of software, hardware, and firmware. In one embodiment, the system is implemented as a number of software modules that comprise computer executable code for performing the functions described herein. In one embodiment, the computer executable code is executed on one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

The foregoing and other variations understood by a skilled artisan can be made to the embodiments described herein without departing from the spirit of that which is disclosed herein. With the understanding therefore, that the described embodiments are illustrative and that the scope is not limited to the described embodiments, certain embodiments are described below with reference to the drawings.

A secure portable reference to individual patient medical data provides a compact, secure, seamless method for a person or entity, including patients or doctors, to access online personal and medical information. The secure portable reference may be a data format and network access device embodied in various methods, apparatus, devices, computer readable media, or kits. For example, in one embodiment, when a patient or doctor requires online access to medical information, the MDR provides an encrypted set of data including a link URL, an identification number for the patient, a hospital identifier, a timestamp, and records this information into a file on a portable storage media or device, such as a USB thumb drive. The secure portable reference may also be transmitted via email to the patient or doctor, for example as an attachment to the email or within the body of the email itself. Also included on the portable storage media is a linking module similar to a web-browser, and a security program that can decrypt the reference set of data. The entire set of data on the portable storage media is called a secure portable reference.

The encrypted data is encrypted using a PIN told to or selected by the patient, doctor, or MDR. By entering the PIN, the security module can decrypt the encrypted portion of the secure portable reference and make it accessible by the linking module.

After decryption, the linking module, which runs on a client computer, then opens the link URL in the reference set of data, and requests the MDR website or Internet resource contained within the URL. The website then authenticates the patient or doctor by having the user enter their PIN. If the PIN matches the data stored by the MDR, the website allows access to the medical records. The medical records data, along with an optional imaging viewing program, are then downloaded by the user to the client computer for consumption. The data transferred can be in any format, including DICOM images, records, and studies and non-DICOM formats.

System Overview

FIG. 1 depicts one embodiment for creating a secure portable reference to medical information, wherein a medical data provider 103 has a medical data repository (MDR) 104. This repository 104 usually consists of multiple PACS, relational databases, imaging modalities, billing systems, or other digital means of storing information, and computer processors to manage access to the data.

When a patient or doctor requests all of a patient's medical information, or a subset thereof, the patient or doctor, user 106, or MDR, selects a PIN 107 or password (for simplicity, called a PIN) which consists of a string of digital characters. The PIN 107 is entered into the MDR 104 directly by the user, or alternatively entered onto the Portable Storage Media and transferred electronically to the MDR 104. The MDR 104 stores the PIN for future reference.

In another embodiment, the MDR generates one PIN, and the user generates another separate PIN that is not transferred to the MDR. The MDR's PIN is stored inside the encrypted information in the secure portable reference, and the user's PIN is never recorded. Instead, the user's PIN is only used to decrypt the information in the secure portable reference. The MDR's PIN that is stored in the secure portable reference is used as the PIN to access the network resource. This embodiment enables the user to keep their selected PIN secret from the MDR, thus enhancing their security.

In another embodiment, the MDR may encrypt multiple PINs into the secure portable reference. In this embodiment, after a first MDR PIN is used to access medical information, it is no longer accepted by an MDR, instead a different MDR PIN in the reference may be used. In this manner, each PIN may only be used once, creating more security and control for the MDR. Additionally, multiple MDR PINs encrypted in a secure portable reference could also be used to access multiple network resources, each with a different PIN set by the MDR.

After entering the PIN 107, the MDR 104 sends to a portable storage media device 101 in step 102 a secure, portable reference to an individual patient medical record called a secure portable reference. The communications channel for the information exchange between the portable storage media device 101 and the MDR 104 can be via computer network, such as an 802.11 wireless connection or Ethernet, or via a local information exchange interface such as Universal Serial Bus or Bluetooth. Any digital communications method can be used.

Portable storage media 101 can be any medium that allows a user to transport and access digital information quickly and easily. Examples of such media include, for example, a USB thumb drive, a flash memory card, a CD or DVD-ROM, a cell phone or mobile device, a magnetic card strip similar to a credit card, and paper printed with a bar code. Similarly, an RFID that allows for storage of a secure portable reference could also act as portable storage media 101. The media need only be able to store and access digital information while remaining transportable by a human carrier.

Example Embodiment of a Secure Portable Reference

Figure 2:
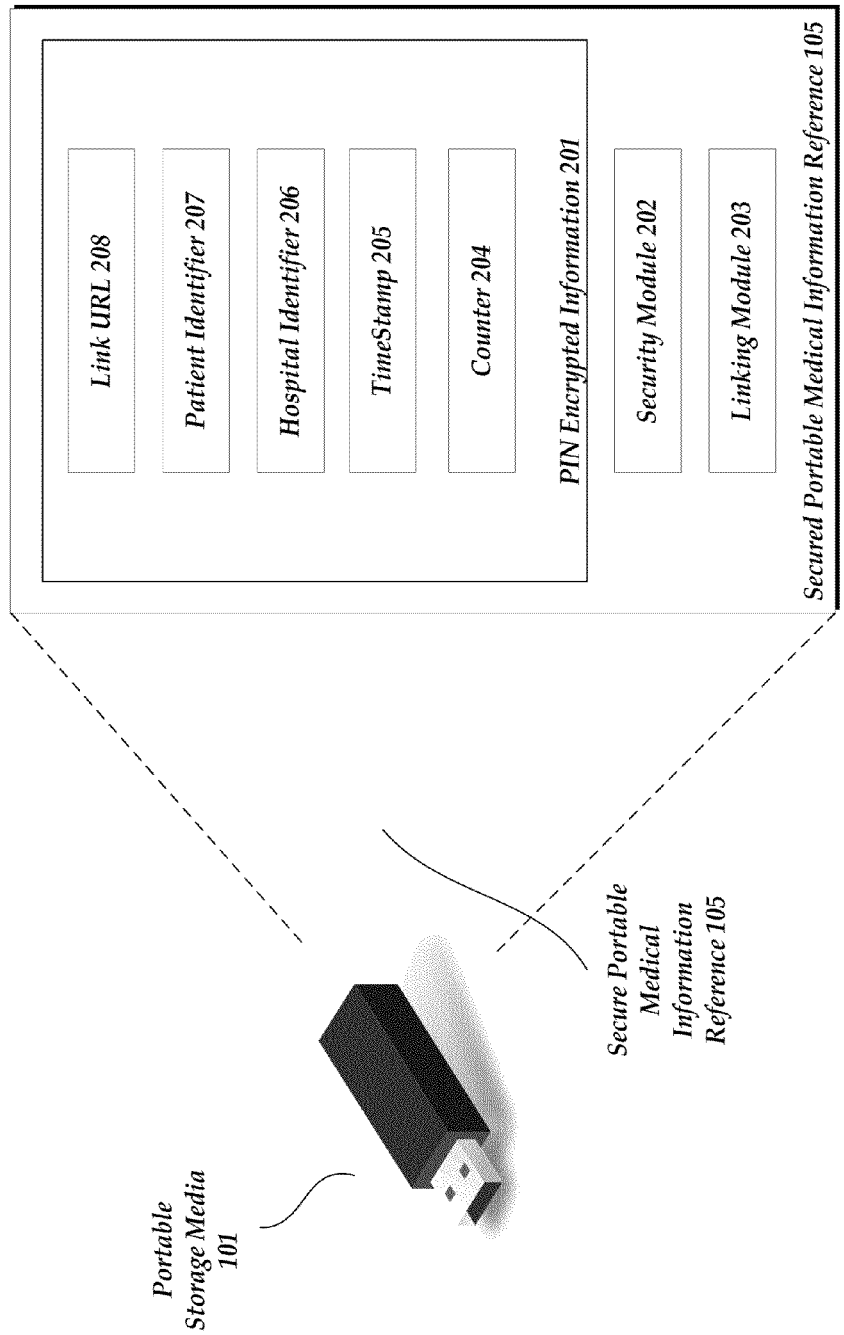
FIG. 2 is a block diagram representing exemplary component parts of a secure portable reference to medical data.

As depicted in FIG. 2, the secure portable reference 105 itself may be partially encrypted 201 by using the PIN 107 entered by the user 106. The encryption can be any method of two way or symmetric key encryption with a shared secret, including AES, Twofish, Blowfish, and 3DES among others. A skilled artisan could also use a public/private key encryption system for the same purpose. The encryption renders any loss of the portable storage media 101 harmless unless the finder knows the PIN 107. The encryption can be done by the MDR before the information is copied to the portable storage media 101. In another embodiment, the encryption is done by the portable storage media itself after a user enters the PIN.

The encrypted information in the secure portable reference 105 may include a link URL 208, a patient identifier 207, a hospital identifier 206, a timestamp or date 205, and a counter 204. In another embodiment, the information is not encrypted, and no security module is used. Instead, the security mechanism is the PIN recorded on the MDR's information systems that, when sent by the user through the client device to the MDR unlocks the requested medical data.

The link URL 208 is the only required information to exist in the secure portable reference 105. It contains the link URL 208 data string, or other Internet resource identifier, where the patient's medical information can be found. The link URL 208 need not point to a resource on the Internet, and may disclose only a network resource on a private network. Further, the link URL 208 may be implicit, such as only the ID of a specific patient in the MDR, if combined with a network resource already known to the linking module 203. Further, in another embodiment, the link URL may include an additional PIN that is to be used for interaction with the MDR. In this way, there would be two PINs: one to unlock the information on the secure portable reference, and another PIN to be given to the MDR when access to the medical information is requested. The user, doctor, or patient need not know the PIN that interacts with the MDR. The MDR may encode it and encrypt it without ever notifying the user. In this embodiment, the second PIN would be sent when the link URL 208 is requested by the client device, enabling the application server to skip the PIN request step.

Further, there may be more than one link URL 208 within a portable secure reference. Often patients and doctors must access multiple studies from different MDRs. By having a plurality of link URLs, each piece of data to be accessed can be referenced, even if they are stored in multiple MDRs. These link URLs may be processed sequentially or in parallel by a client device running the linking module, or in the alternative, only process and access a subset of the link URLs provided in the secure portable reference.

The patient identifier 207 is a unique identifier representing a specific patient in the MDR. This could include a social security number, driver license number, or a uniquely assigned string of characters by the MDR 104. The actual identifier used is not limiting so long as it is unique. Further, any patient identifier could be included in a unique link URL 208, and need not be provided in the secure portable reference. Additionally, the MDR 104 need not provide the patient identifier 207, nor must it be unique to the MDR 104. For example, a group of affiliated MDRs may share the same patient identifiers 207, so long as they are unique between patients. Alternatively, the patient identifier 207 can specify a unique study or exam, or portion of a patient's medical data instead of a patient. In this case, the MDR would return only that portion of medical data corresponding to the identifier.

Similar to the patient identifier 207, the hospital identifier 206 is an optional identifier that uniquely identifies a hospital or MDR where the data is stored. The hospital identifier 206 may be implied as a part of link URL 208 and need not be encrypted separately or included in the secure portable reference, so long as the link URL identifies from which MDR 104 or specific server within an MDR 104 the patients' medical information can be obtained.

A timestamp 205 may be part of the secure portable reference 105. It contains either the time that the secure portable reference 105 was transferred to the portable storage media 101, the date the secure portable reference was last used, or the date the secure portable reference 105 will expire. Alternatively, the secure portable reference 105 could contain multiple time stamps or no time stamps depending on whether the embodiment expires secure portable references based on time. A timestamp can consist of a date, date and time, or time period recognized in any standard time format such as ISO 8601 or UTC. This field can be updated or created by the security module 202 each time the link URL is used to access medical data.

An integer counter 204 can also be included to store the number of times access to medical data with the link URL 208 has occurred, or the maximum number of times access is allowed to occur. This field can be updated or created by the security module 202 each time the link URL is used to access medical data.

The security module 202 comprises hardware or software program instructions that can decrypt the PIN encrypted information 201 for use by the linking module. The person accessing the medical records enters the PIN into the security module for decryption.

The linking module 203 consists of software that either opens up a web browser (such as, for example, Internet Explorer, Firefox, Safari, or Google Chrome) or other network resource consuming application that already exists on a client computer, or comprises a browsing application itself. The linking module instructs the browsing application to access the link URL 208. The linking module may also already contain a custom URL that corresponds to the MDR supplying the medical record. In this case, the linking module 203 need only use the link URL 208 to identify the specific patient, record, or images to be accessed, instead of the network resource location to be accessed.

Example Scenario of Use of Secure Portable Reference

One example scenario will now be discussed with respect to FIG. 3, which shows a sample embodiment for using a secure portable reference.

Figure 3:
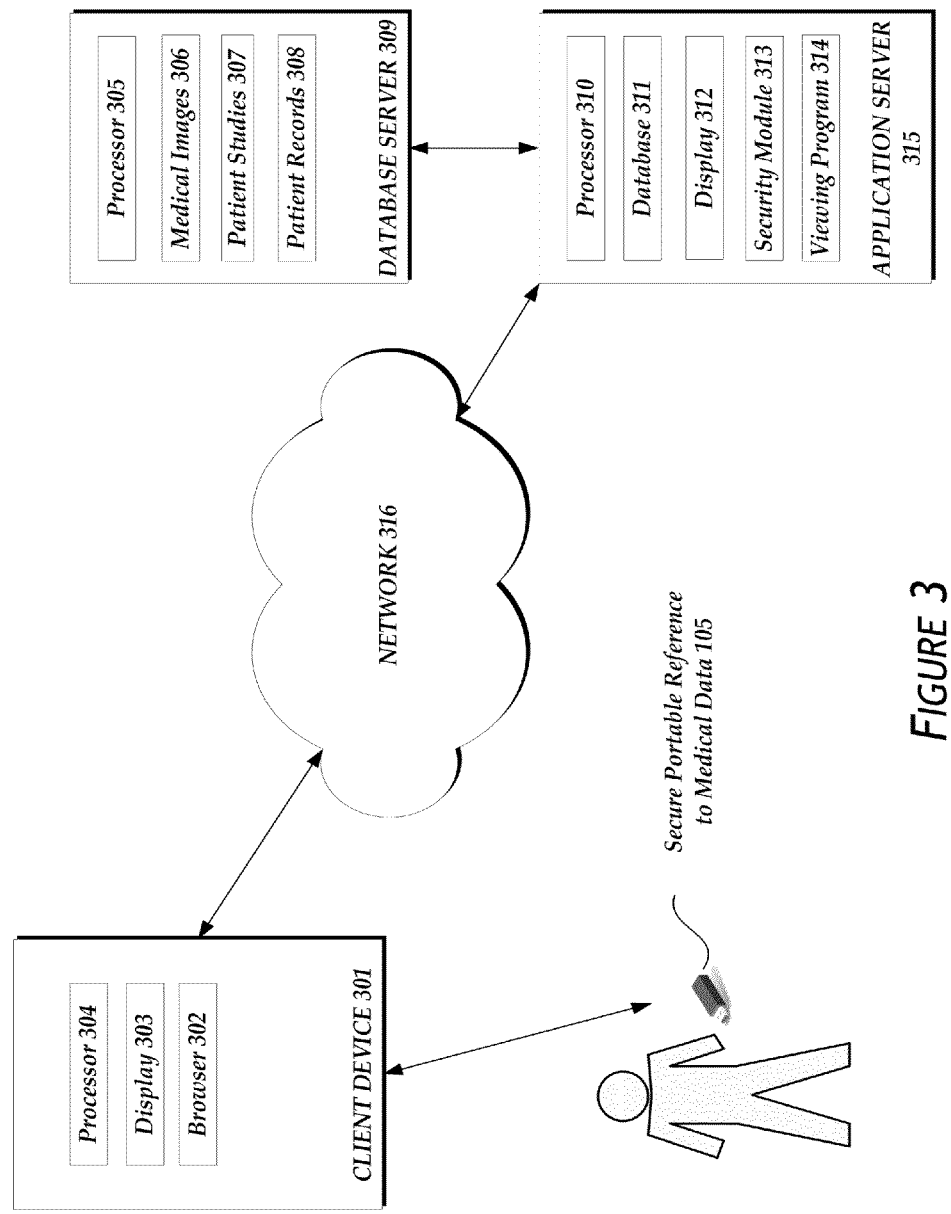
FIG. 3 is a block diagram representing exemplary component parts required for using a secure portable reference to access medical data.

As depicted in FIG. 3, the secure portable reference interacts with a client device 301. The client device can be a portable electronic device, mobile phone, laptop, desktop computer, server, kiosk among other computing devices. The client device may have a computer processor 304, a display device 303, a network resource browser 302, and an interface to read from the portable storage media. Alternatively, the browser may be supplied by the linking module 203. Further, the client device 301 may be connected to, or have the ability to connect to, a computer network such as the Internet, or a private computer network. The secure portable reference is readable by the client device 301 via any wireless or wired communication including USB, Bluetooth, 802.11, Ethernet, or any other data communications method such as a magnetic card reader or an RFID scanner. The client device runs the security 202 and linking modules 203 on the secure portable reference 105, or alternatively uses encryption and linking software already available in its local storage. The client device 301 communicates via the network 316 to the MDR's 104 application server 315. In other embodiments, the client device may communicate directly with the MDR's 104 database server 309.

The application server 315 is controlled by the MDR 104, or any other entity affiliated with the MDR 104. It contains a processor 310 for running program instructions, a database 311 to temporarily store information from the database server 309, a display 312 to configure the application server by administrators, a security module 313 for authenticating and authorizing the secure portable reference, and a medical data viewing program 314. Only the processor 310 and security module 313 are necessary components for the application server 315 to carry out its desired function, and the security module may be move to or combined with any system in the MDR that carries out the security function.

The database server 309 is controlled by the MDR 104, or any other entity affiliated with the MDR 104. It contains the medical images 306, patient records 308, patient studies 307, or any other medical information that is to be accessed by the user. The database server 309 and application server 315 may be running on the same computer or hardware. The database server 309 provides the application server 315 with the medical information to be sent back to the client device 301.

The communication between the client device 301, application server 315, or database server 309, may be performed using the HTTP protocol, or any variety of other networking protocols including encryption, such as ebMS OASIS/ebXML, HTTPS, TCP, IP, CDA HL7, MIME, SMTP, MIME Multipart/Related Content-type, SQL, HL7 Version 2.5, HL7 Version 2.3.1. It may also include any local bus protocols if the database and application servers are functioning on the same computer system. The network communications between servers and devices can be encrypted using a protocol such as SSL, TLS, or any VPN technology that provides for confidentiality.

Accessing Medical Information Using the Secure Portable Reference

Figure 4:
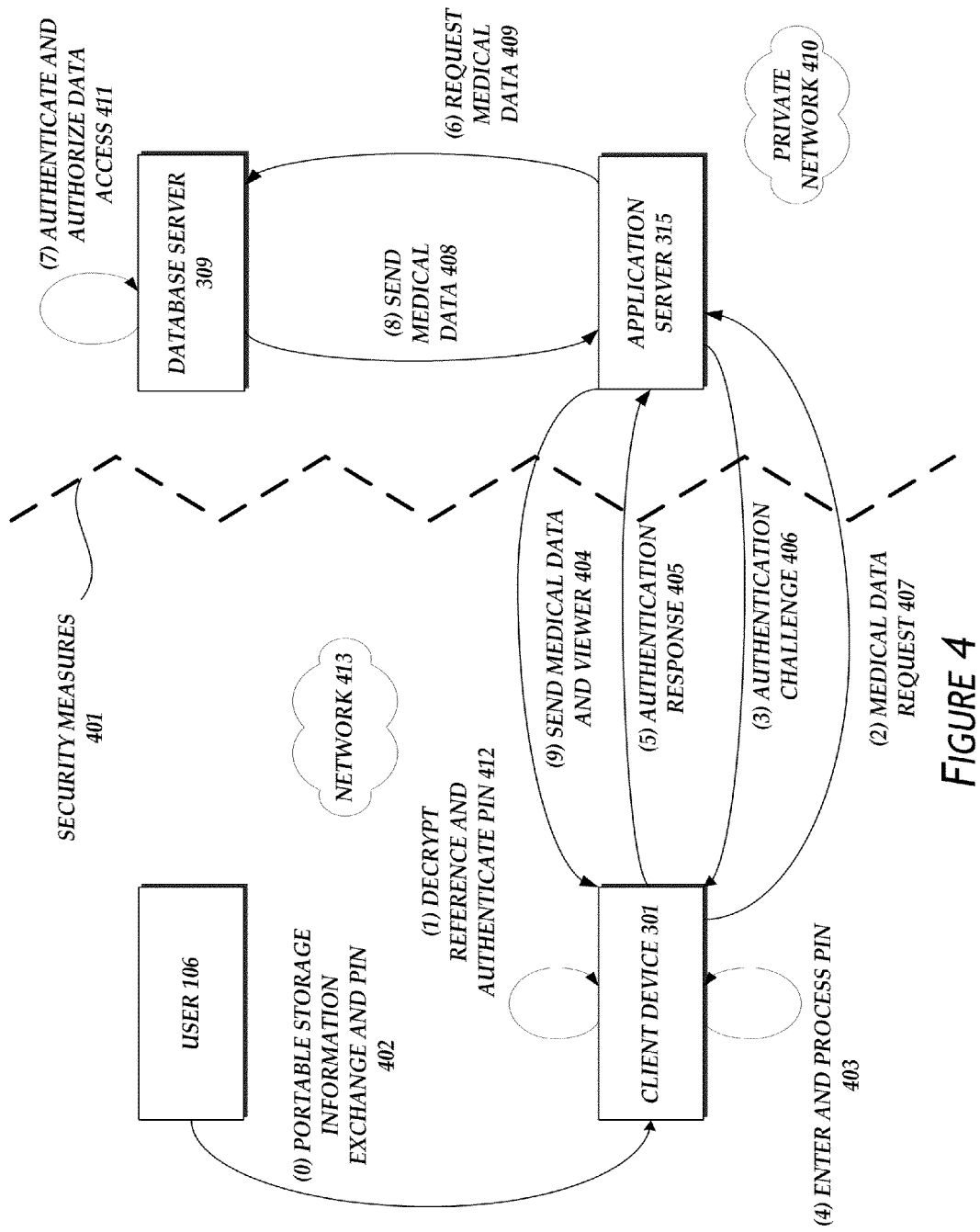
FIG. 4 is a flow diagram representing an exemplary process for access control to medical information using a secure portable reference.

FIG. 4 illustrates an embodiment of a flowchart showing one method (for example, a computer implemented method) of using a secure portable reference to access medical information.

Figure 9:
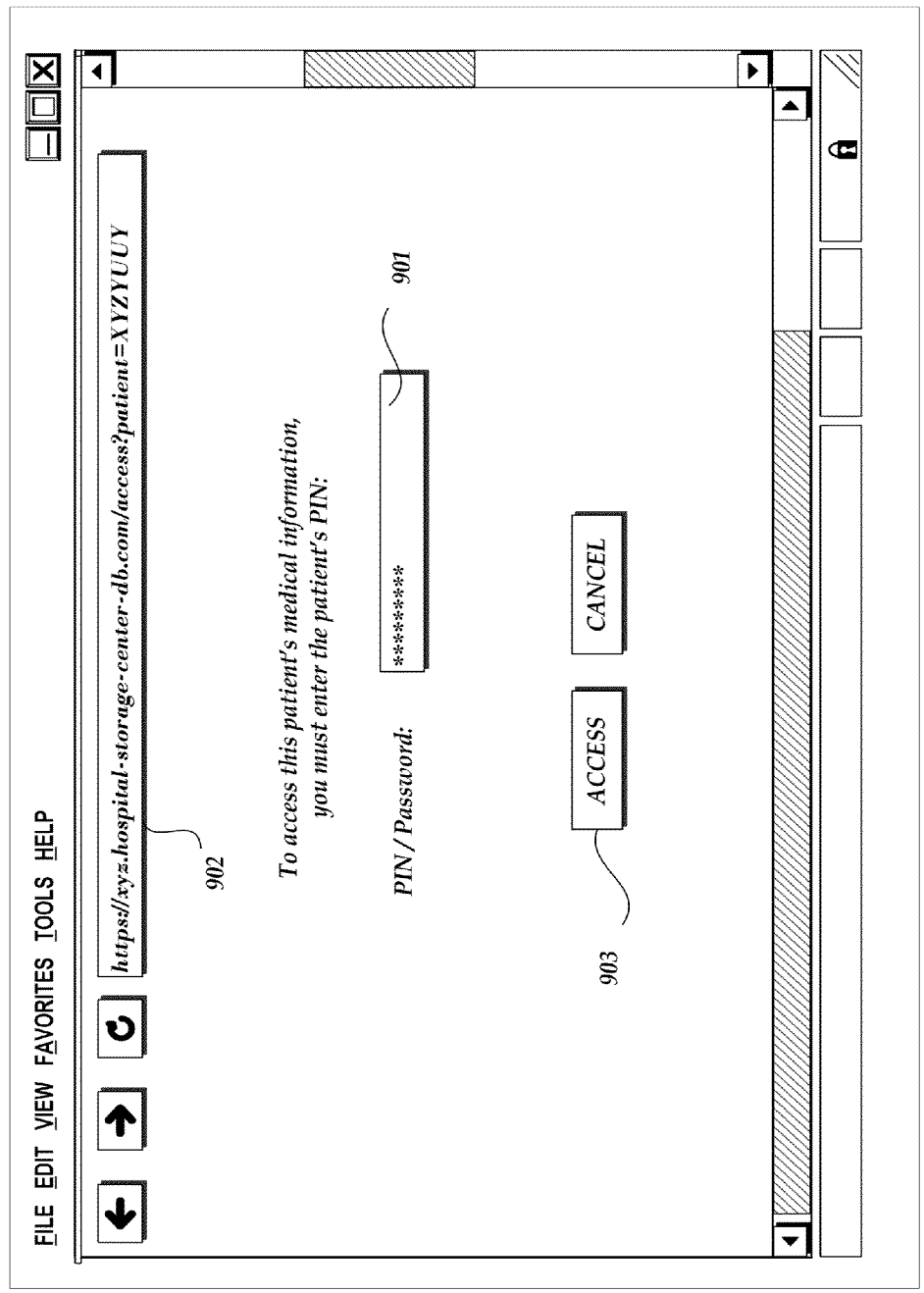
FIG. 9 is an illustrative user interface displaying information for use in accessing medical data using a secure portable reference.

As depicted in FIG. 4, a user 106 can access the medical information by sending the information stored on the portable storage reference 105 with the PIN 107 to the client device 301. One way this can occur is by reading the portable storage media 101. The client device authenticates the PIN by decrypting the reference information 412. After decrypting the link URL 208, client device 301 accesses the network location indicated by the link URL, and sends a medical data request 407 to the application server 315. During this step, the application server 315 and the client device 301 may negotiate SSL or TLS, or some other confidentiality protocol. The application server 315 sends back an authentication challenge 406 to the client device. This challenge 406 can consist of a web page requiring the PIN to be entered such as depicted in FIG. 9. It could also be a public/private key encryption challenge exchange. The client device 301 sends back the authentication response 405 to the application server 315. In the current embodiment, the request 409 is forwarded by the application server 315 to the database server 309 along with the PIN for authentication and authorization 411. If authorized, the database server 309 sends back to the application server 315 the requested medical data 408. In another embodiment, the application server 315 does the authentication and authorization by comparing the PIN to data in an internal user database. In yet another embodiment, the application server 315 and the database server 309 are the same system, and only internal non-network communication is required. Finally, the application server 315 send back the medical data 404 to the client device 301. Optionally, a viewer program 404 that the client device can execute can be sent so that the client device can display and interact with the medical data. In another embodiment, the database server 309 can send the medical data or viewer directly to the client device 309. At this point, the medical data requestor, such as a doctor, has access to the medical information and can correctly carry out their job function such as performing an exam of the medical images. The confidentiality, authentication, and authorization measures explained above work to satisfy the technical security measures 401 required by many MDRs. These steps, or any subset thereof, can be repeated, or run in parallel, to access multiple link URLs that are present in a secure portable reference.

Using the Secure Portable Reference on a Client Device

Figure 5:
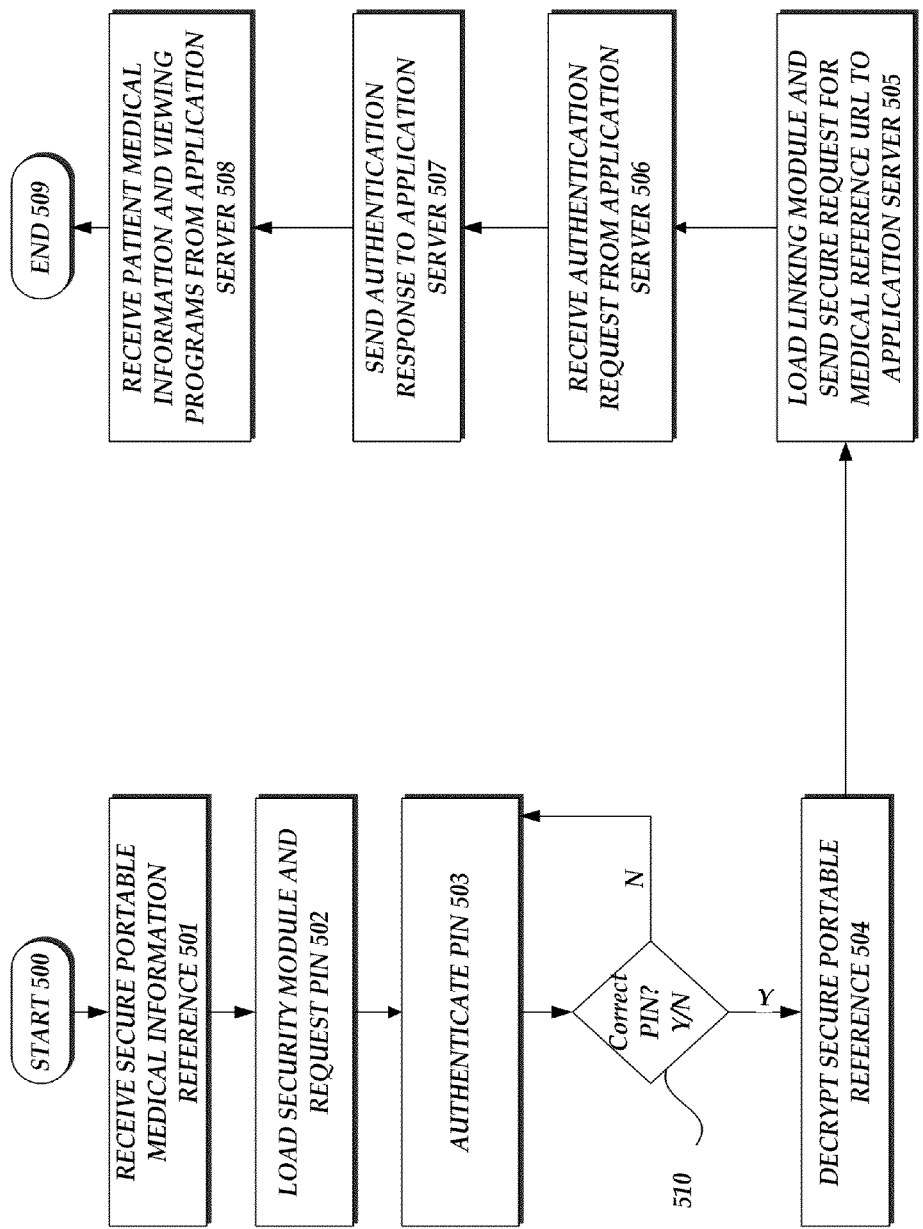
FIG. 5 is a flow diagram representing an exemplary process for a client or browsing device to access medical data using a secure portable reference.

FIG. 5 illustrates an embodiment comprising a method (for example, a computer implemented method) of using the secure portable reference on a client device to securely request and access medical information.

FIG. 5 represents a method taken by a client device when attempting to access medical data referred to by the secure portable reference. First, in one embodiment, the client device receives the secure portable reference 501. In another embodiment, the portable storage media 101 can be read directly by the client device's processor 105 and there is no need for a transfer to occur. Access is readily available to it using local computer data access interfaces. In yet another embodiment, the portable storage media 101 can act as the client device, such as with a smartphone.

The client device's processor then loads the security module and requests the user's PIN 502. After the PIN has been received by the client device, the security module running on the client device authenticates the PIN 503. Any method of authenticating the PIN can be used. For example, one embodiment would attempt decryption of the reference 105. If the reference is successfully decrypted using the PIN, then the PIN has been authenticated. In another embodiment, the PIN would be scrambled using a hashing algorithm (such as SHA or MD5) and stored in the unencrypted area of the secure portable reference 105. Only by hashing the user entered PIN and comparing the hashed values would authentication take place. If the PIN is correct and authenticated 510, the security module running on the client device decrypts 504 the encrypted portion of the secure portable reference 105.

The linking module is then loaded 505 into the client device's processor for execution. The actual order of the loading of the security and linking modules can take place in any order, and occur at any time prior to their needed execution. The client device 301 sends 505 a secure request for the medical reference URL to the application server. The security of the request can be provided by any of the methods discussed above under FIG. 4. The client device 301 then receives an authentication challenge from the application server 506, and responds to the application server 507. The method of the challenge and response can occur in any of the ways discussed above. The client device 301 then receives the patient's medical information and optional viewing program 508 from the application server. The client device 301 can then view the medical data and DICOM or non-DICOM images, and assist the patient in viewing their information. Alternatively, a doctor or medical personal can use the medical data through the viewer to make a diagnosis for the patient or outside referring hospital.

Using the Secure Portable Reference on an Application Server

Figure 6:
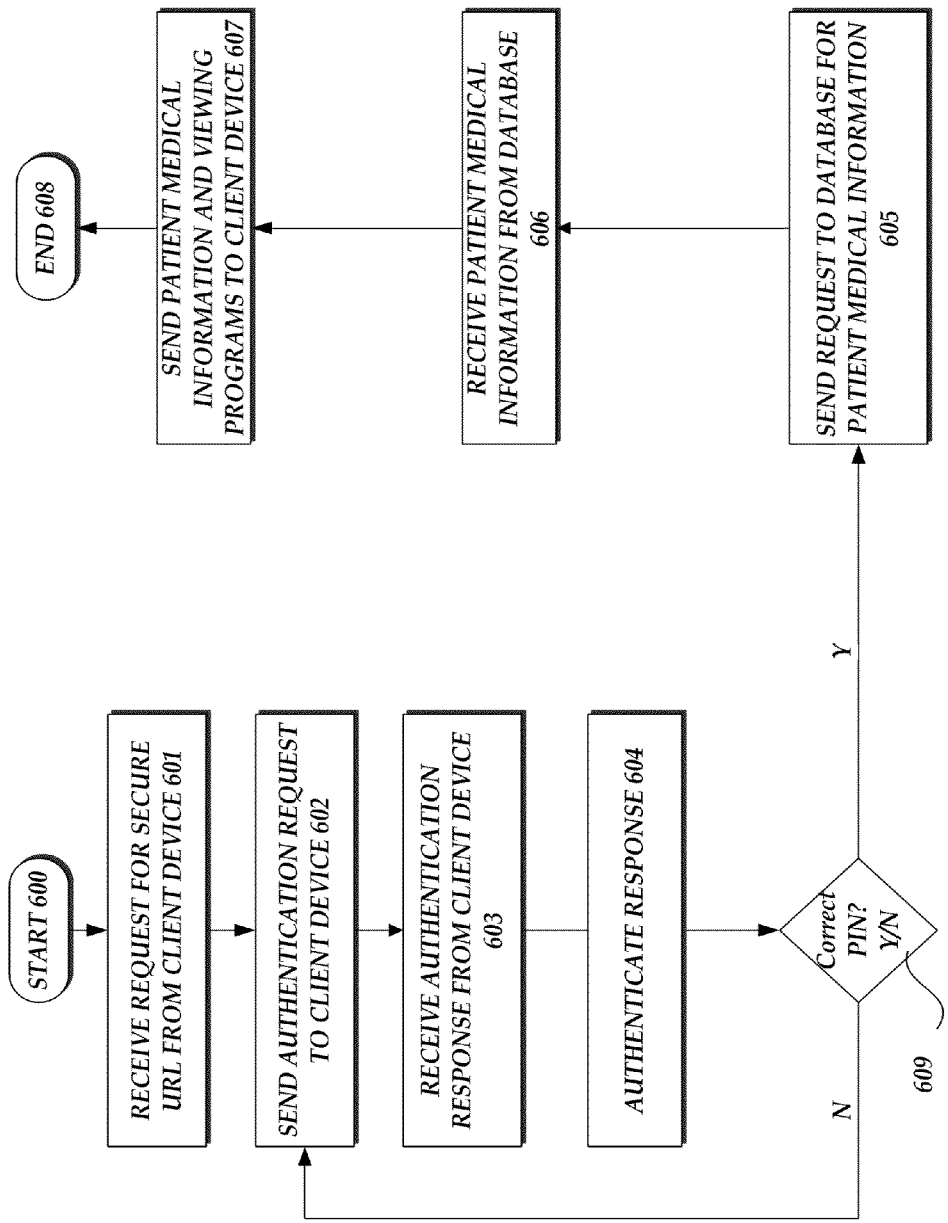
FIG. 6 is a flow diagram representing an exemplary process for an application server to enable access to medical data using a secure portable reference.

FIG. 6 illustrates an embodiment comprising a method (for example, a computer implemented method) of using the secure portable reference at an application server to securely retrieve and send medical information.

FIG. 6 represents a method taken by an application server 315 when responding to requests for medical data originating from a secure portable reference 105. First, the application server 315 receives a request from a client device 301 for specific medical data 601. The application server sends an authentication request to the client device 602. This can be as simple as sending an HTML web page over HTTP protocol requesting the PIN 107 corresponding to the secure portable reference 105 as shown in FIG. 9. In other embodiments, the authentication request can occur using any of the security schemes discussed above, including TLS, SSL, private/public key encryption, encrypting a challenge phrase that is decrypted with the PIN 107, or any method suitable for authentication based on a shared secret. The application server 315 then receives a response from the client device 603, and authenticates the response. In one embodiment, the PIN 107 recorded by the MDR 104 and associated with the secure portable reference 105 is compared to the supplied PIN. If the PINs match, the user and the request are authenticated. In any embodiment, if the PIN is correct, as determined by the authentication mechanism, and the user of the secure portable reference is authenticated, the application server 315 sends a request to the database server 309 for the medical information 605. In other embodiments, the application server may not authenticate the secure portable reference itself, and instead hand off the PIN or authentication information to the database server 309 to perform the authentication. The application server 315 then receives the patient medical information from the database 606, and sends the patient medical information along with a viewer to view the medical information and medical images 607. In another embodiment, the patient medical information or viewer is sent directly from the database server 309 to the client device 301.

Using the Secure Portable Reference on a Database Server

Figure 7:
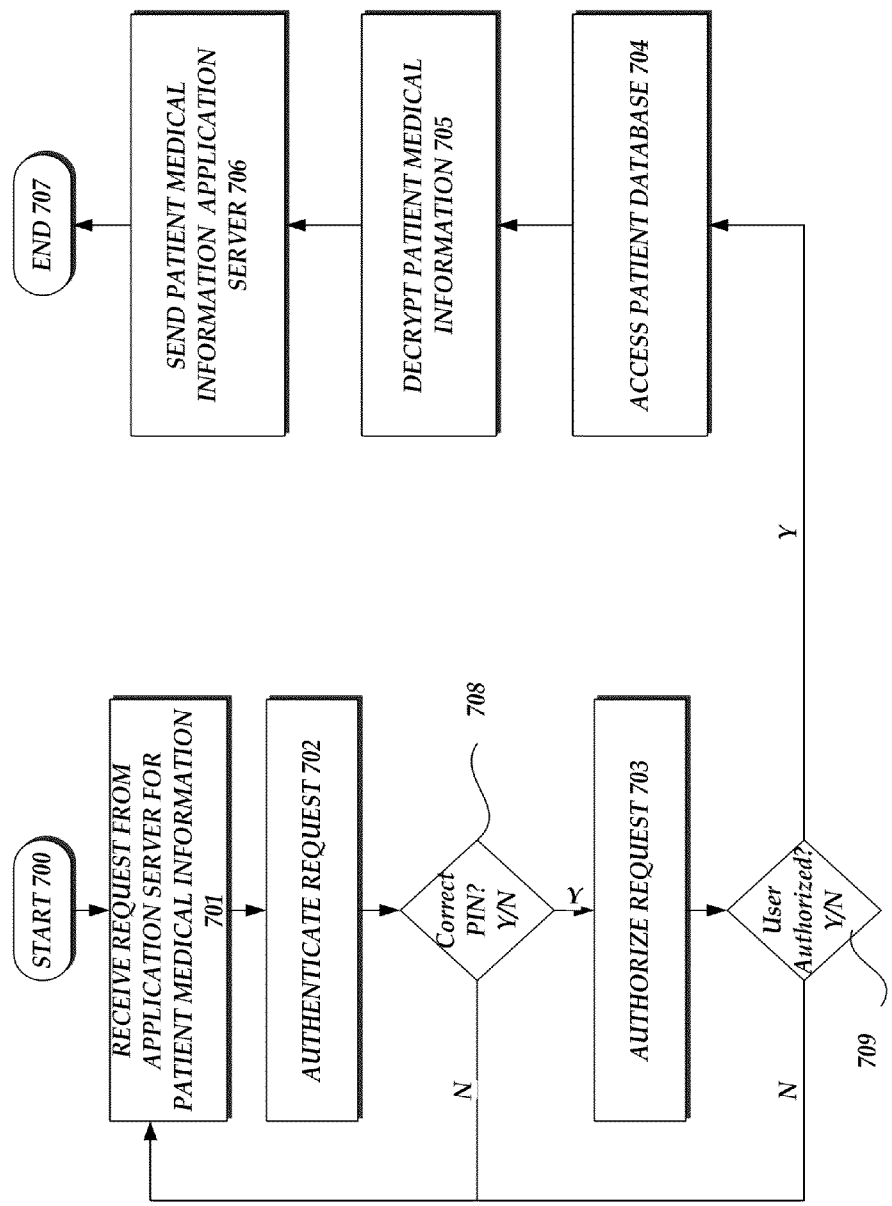
FIG. 7 is a flow diagram representing an exemplary process for a database server to enable access to medical data using a secure portable reference

FIG. 7 illustrates an embodiment comprising a method (for example, a computer implemented method) of using the secure portable reference at a database server to respond to requests for medical information.

FIG. 7 represents a method taken by the database server 309 when responding to requests for medical data and medical images. The database server receives a request from the application server for patient medical information 701. This request includes any authentication information necessary if the database server is to do the authentication of the request. The database server 315 then authenticates the request 702. In another embodiment, the database server does not authenticate the request because the application server has authenticated the request instead, or the request comes from a trusted source. If the request is authenticated and the PIN is correct 708, the request is then authorized 703. In this step, the database server determines if the secure portable reference identified in the authentication is allowed to access the desired medical information. Any method of authorization can be used.

In one embodiment, to determine authorization, the database stores a cross-reference of medical records, images, and data with a patient ID. Only if the patient ID in the secure portable reference 105 that was authenticated is cross referenced with the desired medical record, data or image in the database is the request considered to be authorized 709. If the request is authorized, the database server accesses the requested medical information 704, decrypts the medical information 705 if necessary based on the PIN provided by the request or another key associated with the data to be decrypted, and sends the information back to the application server 706. The decryption can be done using any symmetric encryption method based on the PIN or any other shared secret. In one embodiment, the patient medical information is not encrypted, so the decryption step would not be necessary. The database server 309 may also send encrypted data that can be decrypted by the client device 301 using the PIN 107, another shared secret, or public/private key cryptography. In another embodiment, the patient medical information can be sent back directly to the client device 301 instead of to the application server.

The database server may operate in a number of ways. One embodiment may use, for example, the Content Addressable Storage mechanism provided for in provisional patent application 61/327,556, filed Apr. 23, 2010, incorporated herein by reference and attached in an Appendix.

Alternative Embodiment of Secure Portable Reference on a Database Server

Figure 8:
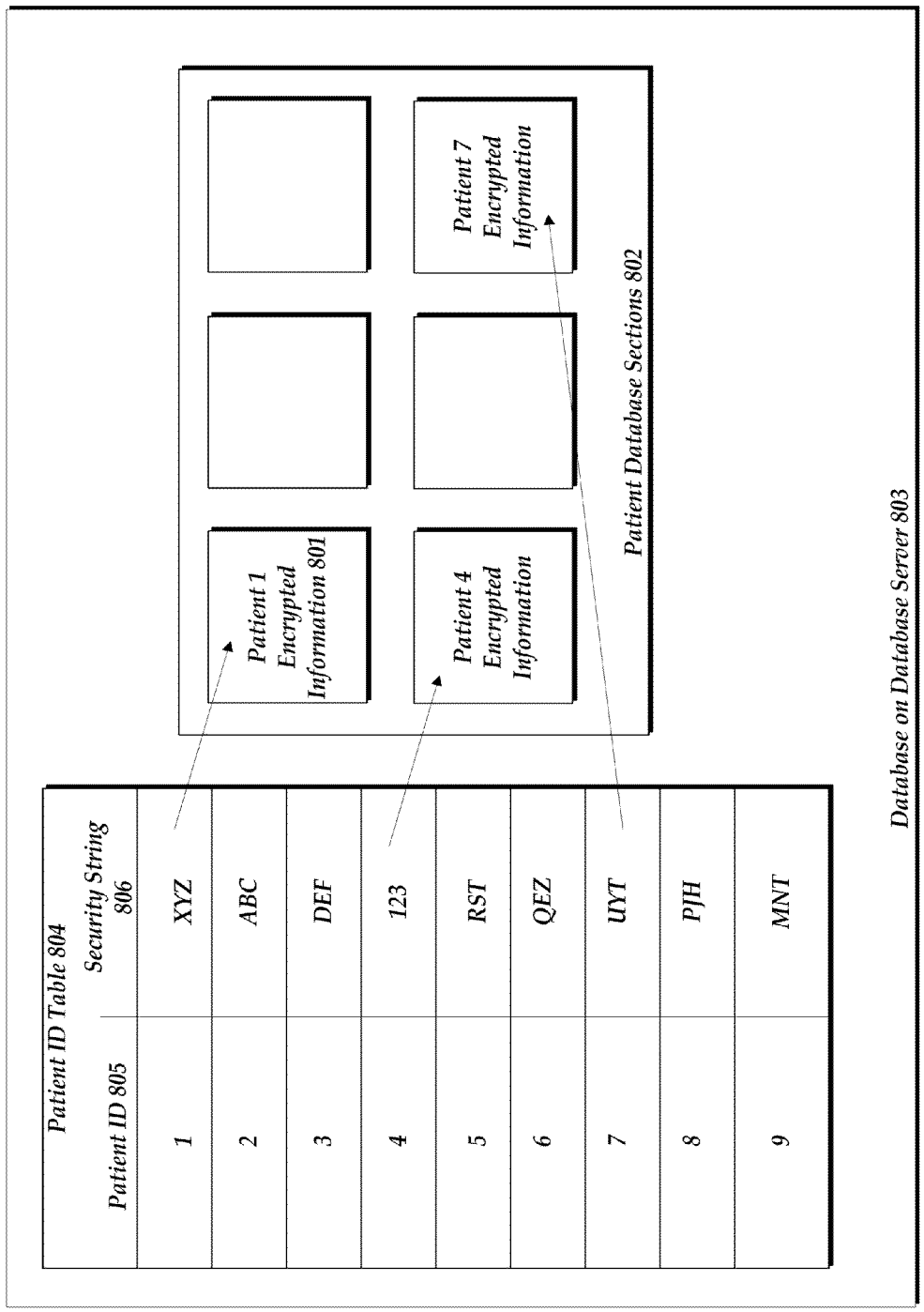
FIG. 8 is a block diagram representing exemplary database components used for secure access to a patient's medical information.

FIG. 8 shows another possible embodiment of the database server configuration. In that embodiment, the patient ID 805 identified in a request for medical information is cross-referenced with an encrypted security string 806 in a relational database table. When the security string 806 is decrypted using the PIN 107, it points to a location or section of the database that stores the patients encrypted information 802. This protects the patient's information by preventing an unauthorized user from detecting where the patient's information is stored, as well as encrypting the medical data itself. These security requirements may be used for HIPAA and other regulatory compliance.

Example User Interface for Using a Secure Portable Reference

FIG. 9 represents an example user interface and request for medical information to an application server using a secure portable reference. In this embodiment, the request 902 is an HTTP SSL (HTTPS) request that is formed by the linking module 203. In this example, the request consists of the protocol, HTTPS, the example domain name, "xyz.hospital-storage-center-db.com", and the file location on the domain to access, here "access". This information can be stored in the Link URL 208 portion of the secure portable reference. The request also includes a patient id, here "patient=XYZYUUY", that identifies which patient record to pull in the database server, and which PIN in the MDR's database is to be used for comparison. The application server 315 responds by serving an HTTPS response that includes a dialog box to enter the patient's PIN 901, and a submission button that triggers an HTTPS request back to the application server 315 which may include the patient id in a hidden HTML field. A skilled artisan will recognize that this is only one method for information exchange, and there are many ways to formulate network data requests and responses between a client device and an application server, using a variety of protocols.

Computing System

Figure 10:
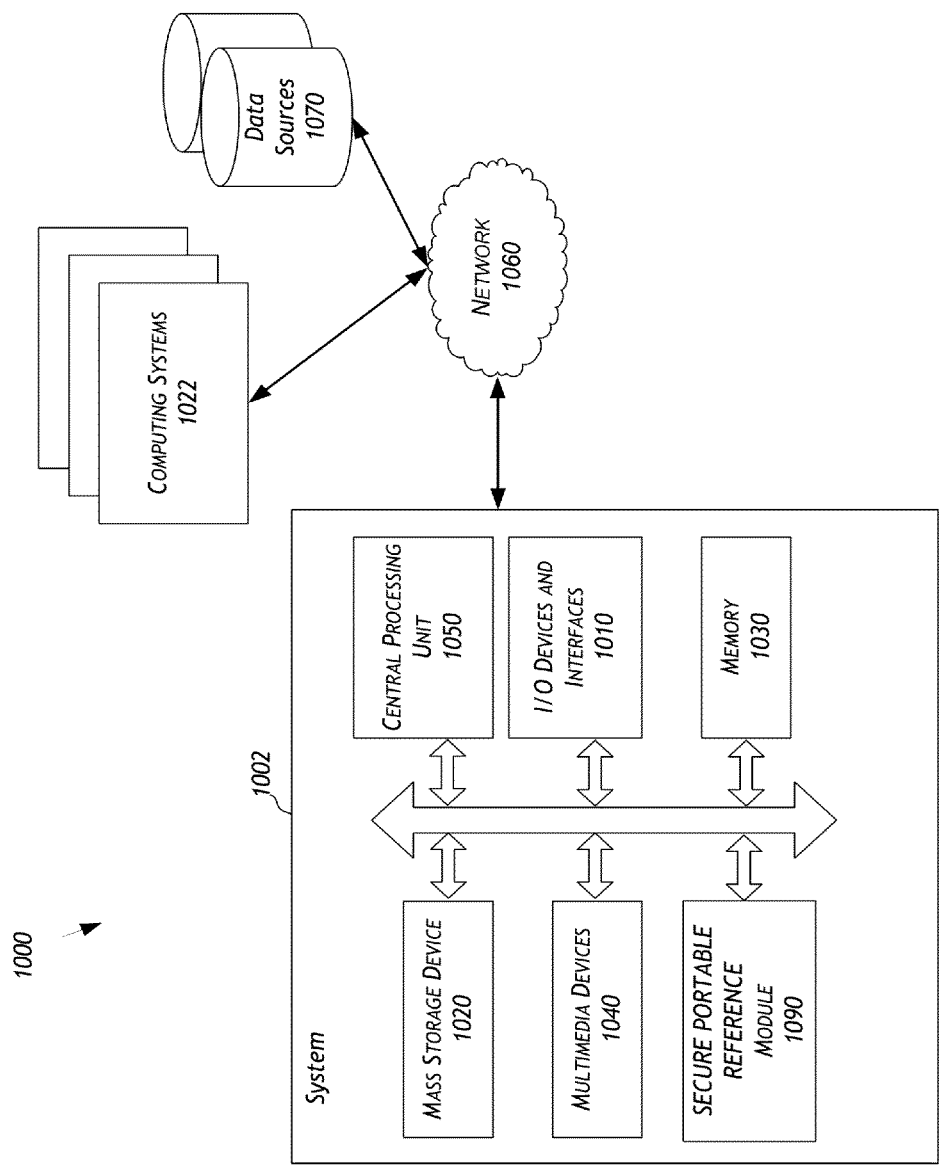
FIG. 10 is a block diagram depicting one embodiment of a computer hardware system configured to run software for implementing one or more embodiments of the secure portable reference and models described herein.

FIG. 10 is a block diagram depicting one embodiment of a computer hardware system configured to run software for implementing one or more embodiments of the secure portable reference systems and models described herein.

In some embodiments, the systems, computer clients and/or servers described above take the form of a computing system 1000 shown in FIG. 10, which is a block diagram of one embodiment of a computing system (which can be a fixed system or mobile device) that is in communication with one or more computing systems 1022 and/or one or more data sources 1070 via one or more networks 1060. The computing system 1000 may be used to implement one or more of the systems, models, and methods described herein. In addition, in one embodiment, the computing system 1000 may be configured to develop and/or generate secure portable reference data. While FIG. 10 illustrates one embodiment of a computing system 1000, it is recognized that the functionality provided for in the components and modules of computing system 1000 may be combined into fewer components and modules or further separated into additional components and modules.

Client/Server Module

In one embodiment, the system 1000 comprises secure portable reference module 1090 configured to carry out the functions, methods, and/or processes described herein. The secure portable reference module 1090 is executed on the computing system 1000 by a central processing unit 1050 discussed further below.

Computing System Components

In one embodiment, the processes, systems, and methods illustrated above may be embodied in part or in whole in software that is running on a computing device. The functionality provided for in the components and modules of the computing device may comprise one or more components and/or modules. For example, the computing device may comprise multiple central processing units (CPUs) and a mass storage device, such as may be implemented in an array of servers.

In general, the word "module," as used herein, refers to logic embodied in hardware or firmware, or to a collection of software instructions, possibly having entry and exit points, written in a programming language, such as, for example, Java, C or C++, or the like. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In one embodiment, the computing system 1000 also comprises a mainframe computer suitable for controlling and/or communicating with large databases, performing high volume transaction processing, and generating reports from large databases. The computing system 1000 also comprises a central processing unit ("CPU") 1050, which may comprise a microprocessor. The computing system 1000 further comprises a memory 1030, such as random access memory ("RAM") for temporary storage of information and/or a read only memory ("ROM") for permanent storage of information, and a mass storage device 1020, such as a hard drive, diskette, or optical media storage device. Typically, the modules of the computing system 1000 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The exemplary computing system 1000 comprises one or more commonly available input/output (I/O) devices and interfaces 1010, such as a keyboard, mouse, touchpad, and printer. In one embodiment, the I/O devices and interfaces 1010 comprise one or more display devices, such as a monitor, that allows the visual presentation of data to a user. More particularly, a display device provides for the presentation of GUIs, application software data, and multimedia presentations, for example. In the embodiment of FIG. 10, the I/O devices and interfaces 1010 also provide a communications interface to various external devices. The computing system 1000 may also comprise one or more multimedia devices 1002, such as speakers, video cards, graphics accelerators, and microphones, for example.

Computing System Device/Operating System

The computing system 1000 may run on a variety of computing devices, such as, for example, a server, a Windows server, an Structure Query Language server, a Unix server, a personal computer, a mainframe computer, a laptop computer, a cell phone, a personal digital assistant, a kiosk, an audio player, and so forth. The computing system 1000 is generally controlled and coordinated by operating system software, such as z/OS, Windows 95, Windows 98, Windows NT, Windows 2000, Windows XP, Windows Vista, Linux, BSD, SunOS, Solaris, or other compatible operating systems. In Macintosh systems, the operating system may be any available operating system, such as MAC OS X. In other embodiments, the computing system 1000 may be controlled by a proprietary operating system. Operating systems control and schedule computer processes for execution, perform memory management, provide file system, networking, and I/O services, and provide a user interface, such as a graphical user interface ("GUI"), among other things.

Network

In the embodiment of FIG. 10, the computing system 1000 is coupled to a network 1060, such as one or more of a LAN, WAN, or the Internet, for example, via a wired, wireless, or combination of wired and wireless, communication link 1070. The network 1060 communicates with various computing devices and/or other electronic devices via wired or wireless communication links. In the exemplary embodiment of FIG. 10, the network 1060 is communicating with one or more computing systems 1022 and/or one or more data sources 1070.

Access to the secure portable reference module 1090 of the computer system 1000 by computing systems 1022 and/or by data sources 1070 may be through a web-enabled user access point such as the computing systems' 1022 or data source's 1070 personal computer, cellular phone, laptop, or other device capable of connecting to the network 1060. The connections may be a direct physical connection, a virtual connection, a physical network connection (for example, using a telephone line or the like) and/or a wireless network connection. Other connection types are also possible. Such a device may have an output module that uses text, graphics, audio, video, and other media to present data and to allow interaction with data via the network 1060.

The output module may be implemented as a combination of an all points addressable display such as a cathode-ray tube (CRT), a liquid crystal display (LCD), a plasma display, or other types and/or combinations of displays. In addition, the output module may be implemented to communicate with input devices 1010 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the output module may communicate with a set of input and output devices 1010 to receive signals from the user.

The input device(s) 1010 may comprise a keyboard, roller ball, pen and stylus, mouse, trackball, voice recognition system, or pre-designated switches or buttons. The output device(s) 1010 may comprise a speaker, a display screen, a printer, or a voice synthesizer. In addition a touch screen may act as a hybrid input/output device. In another embodiment, a user may interact with the system more directly such as through a system terminal connected to the system without communications over the Internet, a WAN, or LAN, or similar network.

In some embodiments, the system 1000 may comprise a physical or logical connection established between a remote microprocessor and a mainframe host computer for the express purpose of uploading, downloading, or viewing interactive data and databases on-line in real time. The remote microprocessor may be operated by an entity operating the computer system 1000, comprising the client server systems or the main server system, an/or may be operated by one or more of the data sources 1070 and/or one or more of the computing systems. In some embodiments, terminal emulation software may be used on the microprocessor for participating in the micro-mainframe link.

In some embodiments, computing systems 1022 who are internal to an entity operating the computer system 1000 may access the secure portable reference module 1090 internally as an application or process run by the CPU 1050.

User Access Point

In one embodiment, a user access point comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

Further, entering any of the modes of operation described herein may include pressing a button, speaking a voice command, performing a gesture with a tracked device, or any other appropriate mechanism.

Other Systems

In addition to the systems that are illustrated in FIG. 10, the network 1060 may communicate with other data sources or other computing devices. The computing system 1000 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

The high-level overview illustrated in FIG. 10 partitions the functionality of the overall system into modules for ease of explanation. It is to be understood, however, that one or more modules may operate as a single unit. Conversely, a single module may comprise one or more subcomponents that are distributed throughout one or more locations. Further, the communication between the modules may occur in a variety of ways, such as hardware implementations (e.g., over a network, serial interface, parallel interface, or internal bus), software implementations (e.g., database, DDE, passing variables), or a combination of hardware and software.

Figure 11:
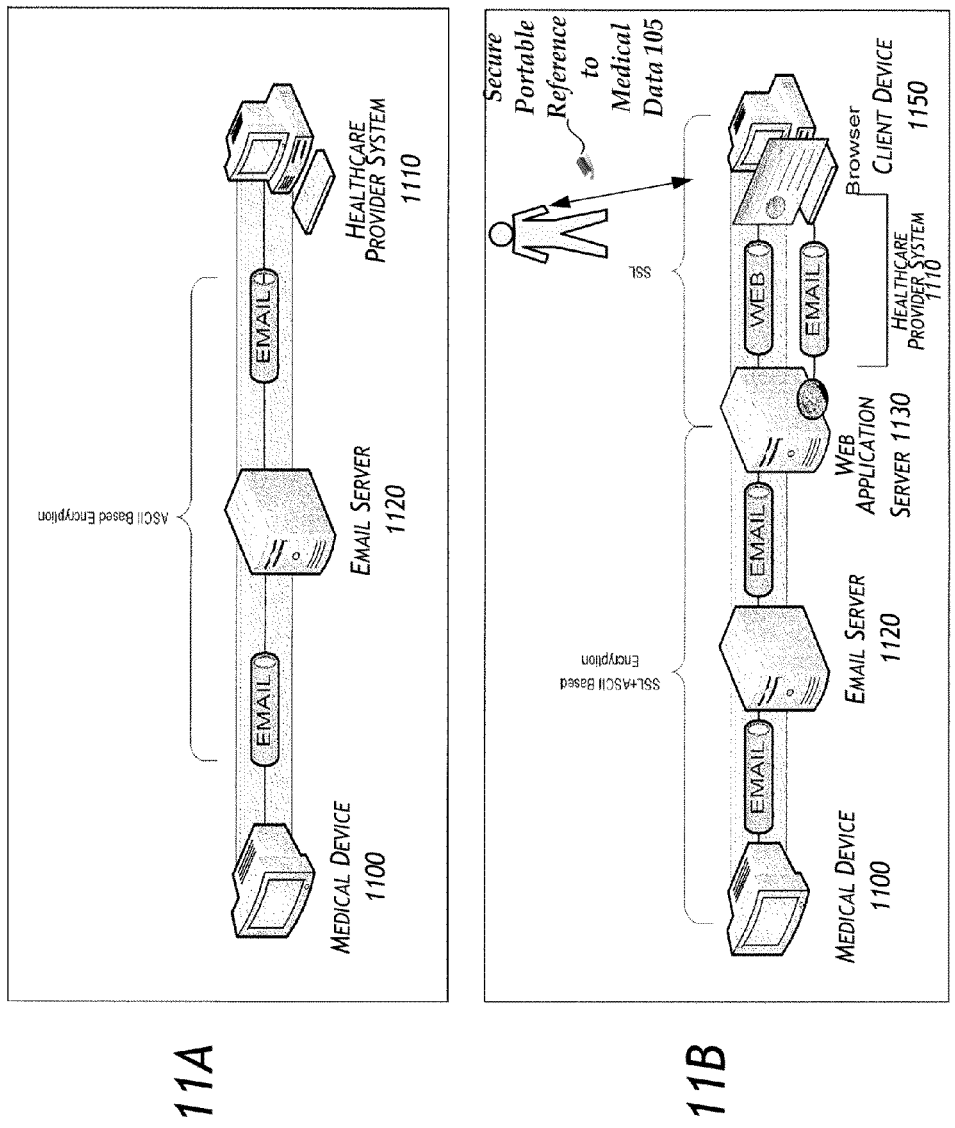
FIG. 11 illustrates one example of architecture for encryption, in accordance with one embodiment of the invention.

Moreover, to comply with HIPAA, data may be communicated in embodiments of the present invention using known encryption and decryption techniques. For example, FIG. 11 shows an exemplary encryption system for one embodiment of the present invention. As shown in FIG. 11 (11A and 11B), communication from medical device 1100 to email server 1120 and communications from email server 1120 and healthcare provider system 1110 may be encrypted using the secure socket level (SSL) protocol. This type of encryption can be used in both embodiments relating to healthcare provider system 1110. That is SSL can be used if healthcare provider system 1110 includes only a client device, as shown in FIG. 11A, or if healthcare provider system 1110 includes an application server and a client device, as shown in FIG. 11B. In the embodiment with the application server, as shown in FIG. 11B, SSL may also be used in communications between the application server and the client device.

Further, as also shown in FIG. 11, on top of the SSL level, all communication from and to medical device 1100 are preferably protected using ASCII based security measures. In one embodiment, three layers of ASCII based security based measures may be used. The first layer may relate to cryptographic hash functions, such as MD5. The second level may relate to data blocking and stuffing. The third level may relate to private-key stream ciphering. Modifications and variations of these layers are possible in embodiments of the present invention. Additionally, a skilled artisan will appreciate that a variety of other encryption algorithms may be used in embodiments of the present invention.

In the particular embodiment shown in FIG. 11B, the application software which runs on the web application server is responsible for at least the following tasks: (1) transforming user selections made via an Internet-connected web browser and a web page into an appropriately formatted request message, such as an email, to send to the designated medical device 1100; (2) sending this request message via the email server 1120 to the medical device 1100; (3) receiving the corresponding reply message, such as an email, generated by the medical device 1100, and parsing this reply message to extract the requested data; (4) storing the extracted data in a database in association with the request message and the healthcare entity that generated the request, and (5) making this data, and other collected data, available via web-based interface on client device 1150.

Additional Embodiments

Another feature in some embodiments of the secure portable reference 105 to medical information is the ability to limit a reference by date or the number of accesses to the medical information. The secure portable reference has a counter field 204, which can be modified by the security module. The counter field can be initialized to hold data to represent the number of times the secure portable reference 105 can be used to access medical data. Each time that the PIN 107 is used to decrypt the information in the secure portable reference, or alternatively each time the link URL is accessed, the counter is decremented by one and the security module re-encrypts the counter. When the counter 204 reaches zero, the security module or the linking module will be unable to request the medical information, thus denying further access to the medical information using the secure portable reference. A skilled artisan would recognize that the counter may be kept and used outside of the secure portable reference for the same purposes, such as the MDR tracking the counter and using it to authorize access to medical data.

Similarly, the secure portable reference may include a timestamp or date 205 that is set by the MDR, doctor, or patient when the secure portable reference 105 is created. The timestamp 205 represents the time after which the security or linking module will be unable to request the medical information. A skilled artisan will recognize that these same limitations do not need to appear in the reference itself for the same functionality to be present. Instead, a counter or timestamp may be kept by the MDR in its database for updating upon access or for comparison. The MDR may also control authorization to the records by referencing the counter or timestamp.

The counter or timestamp functionality allows for the creation of disposable secure portable references and furthers privacy and security goals. By setting a number of maximum accesses or a cutoff date, the secure portable reference, if lost after access has been shut off, cannot be used to gain access to medical records by malicious parties. Further, MDRs can control access to their records using by setting the counter to a single access, thus enabling only one doctor to view the medical data and images, and assuring no others may have access. Such an example embodiment is in effect equivalent to a one-time use, disposable secure portable reference.

The encryption methods referenced throughout this application can be implemented in a variety of ways as mentioned above. One embodiment, for example, can use the System and Method of Encryption for DICOM Volumes provided for in patent application Ser. No. 12/546,611, filed Aug. 24, 2009, incorporated herein by reference and attached in an Appendix.

In some embodiments, when the portable storage media 101 is entered into a reader or computer processor for access, an autoplay program will execute. The autoplay program may launch, automatically without user intervention, the security mechanism and begin the process of attempting to retrieve the private medical information. The autoplay program may run without further user intervention once the user has input their PIN, for example by automatically executing decryption methods using the PIN, using the secure information on the portable storage media to connect to the MDRs where the individual's medical records are stored, requesting the medical records, receiving the medical records, and displaying the medical records to the user on the reader or computer processor.

In another embodiment, after the database server 309 has authorized the request for images, a system in the MDR such as the application server 315 or database server 309 will reduce the resolution of any images to be transferred to the client device using a compression technique. A skilled artisan will recognize that the compression can be lossy or lossless. The reduction in resolution enables large images to be reduced in size so that they can be transferred across slow network connections without clogging network bandwidth for long periods of time.

In another alternative embodiment, the secure portable reference may be transmitted via email directly to the patient or doctor, for example as an attachment to the email or within the body of the email itself. When the user opens the attachment, the secure portable reference may prompt for a PIN, similar to when the secure portable reference is accessed from a portable storage media. The user would also have the option to download the secure portable reference attachment to a portable electronic device, where it may be accessed later or, for example, copied to a USB thumb drive for later use as described above.

Alternatively, the secure portable reference may be embedded in the email message directly, for example, as a link to a secure website, where the user may be prompted to enter the PIN before being allowed access to the medical records. In another possible alternative embodiment, upon entering the PIN the user will be allowed to download the entire secure portable reference to the client computer, which can then run the linking module as described above to gain access to the medical records.

These email alternative embodiments are just some of the many ways the secure portable reference can be provided to a user. These embodiments also demonstrate an additional secured option to access the patient's medical records, as email accounts typically have their own security and password, creating an additional layer to prevent or deter unauthorized access.

In other alternative embodiments, the secure portable reference may be transmitted to the patient or doctor via text message, SMS, or over the Internet in any variety of channels, including, for example, online social media networks.

In another alternative embodiment, the secure portable reference may be in the form of a bar code that may be transmitted to the patient via email, SMS, over the Internet, over any local network (e.g. Bluetooth, RFID), or by a photograph taken by the patient of the bar code at the time the medical records are requested. Alternatively the bar code may be printed on paper and provided to the patient as a secure portable reference. In this embodiment, a bar code scanning device may be used to scan bar code in order to access the patient's medical records stored in an MDR. Those skilled in the art will appreciate that bar codes provide a secure method of access since bar codes are not in a human-readable format. Furthermore, given the ubiquity of scanning software and devices, this particular embodiment is a relatively inexpensive alternative to provide access to an individual's medical records.

In another alternative embodiment, a secure portable reference in the form of a bar code as described above may further include linking the bar code number to a patient ID or a number corresponding to a medical image in an MDR. In such an embodiment, when the bar code is scanned the particular patient record, or the particular medical image, may be accessed directly. Furthermore, scanning the bar code provided in the secure portable reference may activate a link to a secure website, wherein the user may be prompted to enter the PIN before being allowed access to the medical records. In general, it should be understood that an embodiment of a secure portable reference utilizing a format may be combined with any of the other embodiments described herein. For example, the bar code may be stored on a USB thumb drive, for example as an image file or document stored on the USB drive, which may then be accessed and displayed on, for example, a computer or portable electronic device for scanning. In another example, the bar code may be a printed label affixed to the outside of the USB thumb drive or other portable media.

It will also be apparent to a skilled artisan, in light of this disclosure, that the modules described herein can be combined or divided. For example, a skilled artisan will appreciate, in light of this disclosure, that any two or more modules or components can be combined into one module or component. Thus, referring to FIG. 4, the application server 315 and database server 309 may be combined into a single module that performs all or part of the functions of both modules. Conversely, any one module can be divided into multiple modules. For example, the application server 315 can be divided into multiple modules such that each individual module performs part of the functions of the application server 315 and all of the modules collectively perform all such functions.

Similarly, a number of databases are described herein. A skilled artisan will appreciate, in light of this disclosure, that any two or more databases can be combined into one database and that any one database can be divided into multiple databases.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

The processes, computer readable medium, and systems described herein may be performed on various types of hardware, such as computer systems or computing devices. Any module or unit of embodiments herein may each be separate computing devices, applications, or processes—or one or more may be combined to run as part of one application or process—and/or each or one or more may be part of or run on a computing device. Computing devices or computer systems may include a bus or other communication mechanism for communicating information, and a processor coupled with the bus for processing information. A computer system or device may have a main memory, such as a random access memory or other dynamic storage device, coupled to the bus. The main memory may be used to store instructions and temporary variables. The computer system or device may also include a read-only memory or other static storage device coupled to the bus for storing static information and instructions. The computer systems or devices may also be coupled to a display, such as a CRT, LCD monitor, LED array, e-paper, projector, or stereoscopic display. Input devices may include a mouse, a trackball, touchscreen, tablet, foot pedal, or cursor direction keys.

Each computer system or computing device may be implemented using one or more physical computers, processors, embedded devices, field programmable gate arrays (FPGAs), or computer systems or portions thereof. The instructions executed by the computer system or computing device may also be read in from a computer-readable medium. The computer-readable medium may be non-transitory, such as a CD, DVD, optical or magnetic disk, laserdisc, flash memory, or any other medium that is readable by the computer system or device. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. Transmission of information may be performed on the hardware layer using any appropriate system, device, or protocol, including those related to or utilizing Firewire, PCI, PCI express, CardBus, USB, CAN, SCSI, IDA, RS232, RS422, RS485, 802.11, etc. The communication among modules, systems, devices, and elements may include handshaking, notifications, coordination, encapsulation, encryption, headers, such as routing or error detecting headers, or any other appropriate communication protocol or attribute. Communication may also include messages related to HTTP, HTTPS, FTP, TCP, IP, ebMS OASIS/ebXML, DICOM, DICOS, secure sockets, VPN, encrypted or unencrypted pipes, MIME, SMTP, MIME Multipart/Related Content-type, SQL, etc.

Any appropriate 3D graphics processing may be used for displaying or rendering, including processing based on OpenGL, Direct3D, Java 3D, etc. Whole, partial, or modified 3D graphics packages may also be used, such packages including 3DS Max, SolidWorks, Maya, Form Z, Cybermotion 3D, VTK, Slicer, Blender or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

All of the methods and processes described herein may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware. In addition, the components referred to herein may be implemented in hardware, software, firmware or a combination thereof.

By way of example, some embodiments of the invention may be implemented using conventional personal computers (PCs), desktops, hand-held devices, multiprocessor computers, pen computers, microprocessor-based or programmable customer electronics devices, minicomputers, mainframe computers, personal mobile computing devices, mobile phones, portable or stationary personal computers, palmtop computers or the like. As used herein, the term "computing system" is intended to encompass a single computer or computing device, and is also intended to encompass a collection of computers or computing devices that interact with each other (e.g., over a network). The term "server" is intended to encompass any computing system that responds (or is programmed or configured to respond) to requests by sending or "serving" information. The term "node" is intended to encompass a computing system that is addressable on a network.

The storage media referred to herein symbolize elements that temporarily or permanently store data and instructions. Although storage functions may be provided as part of a computer, memory functions can also be implemented in a network, processors (e.g., cache, register), or elsewhere. Various types of storage mediums can be used to implement features of the invention, such as a read-only memory (ROM), a random access memory (RAM), or a memory with other access options. Further, memory functions may be physically implemented by computer-readable media, such as, for example: (a) magnetic media, like a hard disk, a floppy disk, a magnetic disk, a tape, or a cassette tape; (b) optical media, like an optical disk (e.g., a CD-ROM), or a digital versatile disk (DVD); (c) semiconductor media, like DRAM, SRAM, EPROM, EEPROM, memory stick, and/or by any other media, like paper.

Some embodiments of the invention may also include computer program products that are stored in a computer-readable medium or transmitted using a carrier, such as an electronic carrier signal communicated across a network between computers or other devices. In addition to transmitting carrier signals, network environments may be provided to link or connect components in the disclosed systems. Networking environments are commonplace in offices, enterprise-wide computer networks, intranets and the Internet (i.e., the World Wide Web). The network may be a wired or a wireless network. To name a few network implementations, the network may be, for example, a local area network (LAN), a wide area network (WAN), a public switched telephone network (PSTN), an Integrated Services Digital Network (ISDN), an infrared (IR) link, a radio link, such as a Universal Mobile Telecommunications System (UMTS), Global System for Mobile Communication (GSM), Code Division Multiple Access (CDMA), or a satellite link.

Transmission protocols and data formats are also known, such as, for example transmission control protocol/internet protocol (TCP/IP), hypertext transfer protocol (HTTP), secure HTTP, wireless application protocol, unique resource locator (URL), unique resource identifier (URI), hypertext markup language (HTML), extensible markup language (XML), extensible hypertext markup language (XHTML), wireless application markup language (WML), Standard Generalized Markup Language (SGML), etc. Such features may be utilized to implement some embodiments of the present invention, as disclosed herein.

As apparent, the features and attributes of the specific embodiments disclosed herein may be combined in different ways to form additional embodiments, all of which fall within the scope of the present disclosure. In some embodiments, all of these features and embodiments may be implemented based on the systems, methods and devices described herein.

In some embodiments, all of the described features and modes of operation are present. In other embodiments, however, merely one or more of the described features and modes of operation are present and available.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

While the invention has been discussed in terms of certain embodiments, it should be appreciated that the invention is not so limited. Many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is essential.

Each of the following applications or patents are incorporated herein by this reference in their entirety and made a part of this specification, including provisional patent application 61/327,556, filed Apr. 23, 2010, patent application Ser. No.

12/546,611, filed Aug. 24, 2009, patent application Ser. No. 11/591,889 published as 2007/0050216, filed Nov. 2, 2006, U.S. Pat. No. 7,979,387 filed Nov. 2, 2006, and U.S. Pat. No. 7,783,163 filed Jun. 12, 2009.

What is claimed is:

1. A computer-implemented method for managing access to an individual's medical images using one or more computer processors configured to execute the steps comprising:
generating a first personal identification number for a secure portable reference, the secure portable reference stored within a USB thumb drive;
using the first personal identification number to encrypt secure information used to access an individual's medical digital imaging and communications in medicine (DICOM) images stored on two or more databases;
storing the secure information on the secure portable reference within the USB thumb drive;
storing, in the secure portable reference within the USB thumb drive, a security module configured to decrypt at least a portion of the secure portable reference including the security information;
storing, in the secure portable reference within the USB thumb drive, computer-executable instructions configured to:
receive a second personal identification number from a user through a client computer connected to the USB thumb drive;
use the second personal identification number and the security module to decrypt the secure information stored on the secure portable reference, the secure information being necessary to access the medical images stored on the two or more databases;
request the individual's medical DICOM images from the two or more databases using the secure information stored on the secure portable reference within the USB thumb drive;
receive the individual's medical DICOM images from the two or more databases associated with the secure information stored on the secure portable reference within the USB thumb drive; and
provide a user interface for the client device, configured to in response to receiving the individual's medical DICOM images, process and display the individual's medical DICOM images from the two or more databases associated with the secure information stored on the secure portable reference; and
expiring and rendering unusable the secure portable reference after a configurable number of uses of the secure portable reference to retrieve the individual's medical DICOM images from the two or more databases.

2. The method of claim 1, further comprising:
storing, in the secure portable reference within the USB thumb drive, computer-executable instructions configured to obtain a set of one or more personal identification numbers for the individual for each of the two or more databases;
using the set of one or more personal identification numbers to encrypt the secure information used to access the individual's medical DICOM images stored on the two or more databases;
storing, in the secure portable reference within the USB thumb drive, the set of one or more personal identification numbers in the secure information; and
storing, in the secure portable reference within the USB thumb drive, computer-executable instructions configured to use the set of one or more personal identification numbers when requesting the individual's medical DICOM images from the two or more databases.

3. The method of claim 1, wherein the secure portable reference further comprises at least:
one or more sets of link data, wherein the sets of link data comprise unique resource location information for the individual's medical DICOM images held at two or more databases; and
a linking module configured to enable access to the individual's medical DICOM images using at least the unique resource location information.

4. The method of claim 1, wherein the secure portable reference further comprises within the USB thumb drive all of the following:
a unique identification number for the individual;
one or more distinct identifiers corresponding to two or more databases where the individual's medical DICOM images are stored;
a date recorded timestamp;
a last accessed timestamp;
an expiration date timestamp;
a total access counter to indicate the number of times the individual's medical DICOM images has been accessed; and
an expiration counter to indicate the maximum number of times the individual's medical DICOM images may be accessed.

5. The method of claim 1, wherein generating the first personal identification number comprises selecting the first personal identification number by a user.

6. The method of claim 1, wherein generating the first personal identification number comprises generating the first personal identification number by a medical DICOM images repository.

7. The method of claim 1, further comprising storing the secure portable reference on a single portable storage medium.

8. The method of claim 1, further comprising transmitting the secure portable reference via email.

9. A USB thumb drive comprising a non-transitory computer-readable medium comprising computer-executable instructions for accessing an individual's medical digital imaging and communications in medicine (DICOM) images, said computer-executable instructions, when running on one or more computers, perform a method comprising:
interfacing a secure portable reference associated with an individual to a client device after connection of the USB thumb drive to the client device, the USB thumb drive comprising the secure portable reference;
displaying, within a web browser, a first web user interface for the client device to prompt a user to input a personal identification number;
receiving a personal identification number from the user through the first user interface on the client device interfaced to the secure portable reference;
using the personal identification number and a security module stored in the secure portable reference to decrypt secure information stored on the secure portable reference;
requesting the individual's medical DICOM images from two or more databases associated with the secure information stored on the secure portable reference, the two or more databases requiring the decrypted secure information to allow access to the medical DICOM images;
receiving the individual's medical DICOM images from the two or more databases associated with the secure information stored on the secure portable reference;

in response to receiving the medical DICOM images, displaying within the web browser a second web user interface for the client device, the second user interface configured to display the individual's medical DICOM images from the two or more databases associated with the secure information stored on the secure portable reference; and expiring and rendering unusable the secure portable reference after a configurable number of uses of the secure portable reference to retrieve the individual's medical DICOM images from the two or more databases.

10. The USB thumb drive comprising the non-transitory computer-readable medium of claim 9, wherein the non-transitory computer-readable medium comprising computer-executable instructions for accessing an individual's medical DICOM images, is a single portable storage medium.

11. The USB thumb drive comprising the non-transitory computer-readable medium of claim 9, wherein the secure portable reference is associated with an email message.

12. The USB thumb drive comprising the non-transitory computer-readable medium of claim 6, wherein the secure portable reference comprises at least the following data:

one or more sets of link data, wherein the sets of link data comprise unique resource location information for the individual's medical DICOM images held at two more databases; and a linking module configured to enable access to the individual's medical DICOM images using at least the unique resource location information.

13. The USB thumb drive comprising the non-transitory computer-readable medium of claim 9, wherein the secure portable reference further comprises all of the following:

a unique identification number for the individual;

one or more distinct identification numbers corresponding to two or more databases where the individual's medical DICOM images are stored;

a date recorded timestamp;

a last accessed timestamp;

an expiration date timestamp a total access counter to indicate the number of times the individual's medical DICOM images has been accessed; and an expiration counter to indicate the maximum number of times the individual's medical DICOM images may be accessed.

14. The USB thumb drive comprising the non-transitory computer-readable medium of claim 13, wherein the method further comprises determining that access to the individual's medical DICOM images has expired by comparing the total access counter to the expiration counter.

* * * * *